United States Patent
Shelton, IV et al.

(10) Patent No.: US 9,572,622 B2
(45) Date of Patent: Feb. 21, 2017

(54) BIPOLAR ELECTROSURGICAL FEATURES FOR TARGETED HEMOSTASIS

(71) Applicant: Ethicon Endo-Surgery, Inc., Cincinnati, OH (US)

(72) Inventors: Frederick E. Shelton, IV, Hillsboro, OH (US); Chester O. Baxter, III, Loveland, OH (US); David C. Yates, West Chester, OH (US); John V. Hunt, Cincinnati, OH (US); Kreena R. Modi, Akron, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 871 days.

(21) Appl. No.: 13/709,473

(22) Filed: Dec. 10, 2012

(65) Prior Publication Data

US 2014/0163541 A1   Jun. 12, 2014

(51) Int. Cl.
*A61B 18/14*  (2006.01)
*A61B 18/00*  (2006.01)
*A61B 17/32*  (2006.01)

(52) U.S. Cl.
CPC .... *A61B 18/1445* (2013.01); *A61B 17/320092* (2013.01); *A61B 2018/00005* (2013.01); *A61B 2018/0063* (2013.01); *A61B 2018/00642* (2013.01); *A61B 2018/00702* (2013.01); *A61B 2018/00797* (2013.01); *A61B 2018/00809* (2013.01); *A61B 2018/00815* (2013.01); *A61B 2018/00898* (2013.01); *A61B 2018/1495* (2013.01)

(58) Field of Classification Search
CPC ................... A61B 17/320092; A61B 18/1445; A61B 2018/00005; A61B 2018/0063; A61B 2018/00642; A61B 2018/0072; A61B 2018/00797; A61B 2018/00809; A61B 2018/00815; A61B 2018/00898; A61B 2018/1495
See application file for complete search history.

(56) References Cited

U.S. PATENT DOCUMENTS

| 4,033,356 A * | 7/1977 | Hara .................... A61N 1/0452 607/150 |
| 6,500,176 B1 | 12/2002 | Truckai et al. |
| 6,783,524 B2 | 8/2004 | Anderson et al. |

(Continued)

OTHER PUBLICATIONS

U.S. Appl. No. 61/410,603, filed Nov. 5, 2010, Houser et al.

*Primary Examiner* — Amanda Patton
(74) *Attorney, Agent, or Firm* — Frost Brown Todd LLC

(57) ABSTRACT

An apparatus is configured to operate on tissue. The apparatus includes an end effector with an upper jaw and a lower jaw. The upper jaw is configured to pivot relative to the lower jaw. The apparatus also includes an electrode cap coupled to either the upper or lower jaw. The electrode cap includes a first electrode surface configured at a first polarity and a second electrode surface configured at a second polarity. The second polarity is opposite to the first polarity. The electrode cap is configured to be applied to tissue such that the electrode cap is operable to deliver bipolar RF energy to the tissue. The electrode cap may be used to selectively weld bleeding tissue in a localized fashion, without having to place the tissue between the jaws, and without having to use an instrument separate from the jaws.

20 Claims, 25 Drawing Sheets

(56) References Cited

U.S. PATENT DOCUMENTS

| | | | |
|---|---|---|---|
| 7,112,201 B2 | 9/2006 | Truckai et al. | |
| 7,125,409 B2 | 10/2006 | Truckai et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,309,849 B2 | 12/2007 | Truckai et al. | |
| 7,311,709 B2 | 12/2007 | Truckai et al. | |
| 7,354,440 B2 | 4/2008 | Truckai et al. | |
| 7,381,209 B2 | 6/2008 | Truckai et al. | |
| 7,442,193 B2 * | 10/2008 | Shields | A61B 18/1445 606/49 |
| 8,663,222 B2 * | 3/2014 | Anderson | A61B 18/1445 606/52 |
| 9,039,732 B2 * | 5/2015 | Sims | A61B 17/285 606/207 |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2009/0112202 A1 * | 4/2009 | Young | A61B 18/16 606/33 |
| 2011/0015660 A1 | 1/2011 | Wiener et al. | |
| 2011/0087218 A1 | 4/2011 | Boudreaux et al. | |
| 2012/0078243 A1 | 3/2012 | Worrell et al. | |
| 2012/0078244 A1 | 3/2012 | Worrell et al. | |
| 2012/0078247 A1 | 3/2012 | Worrell et al. | |
| 2012/0078248 A1 | 3/2012 | Worrell et al. | |
| 2012/0116379 A1 | 5/2012 | Yates et al. | |
| 2013/0023868 A1 | 1/2013 | Worrell et al. | |
| 2013/0030428 A1 | 1/2013 | Worrell et al. | |

\* cited by examiner

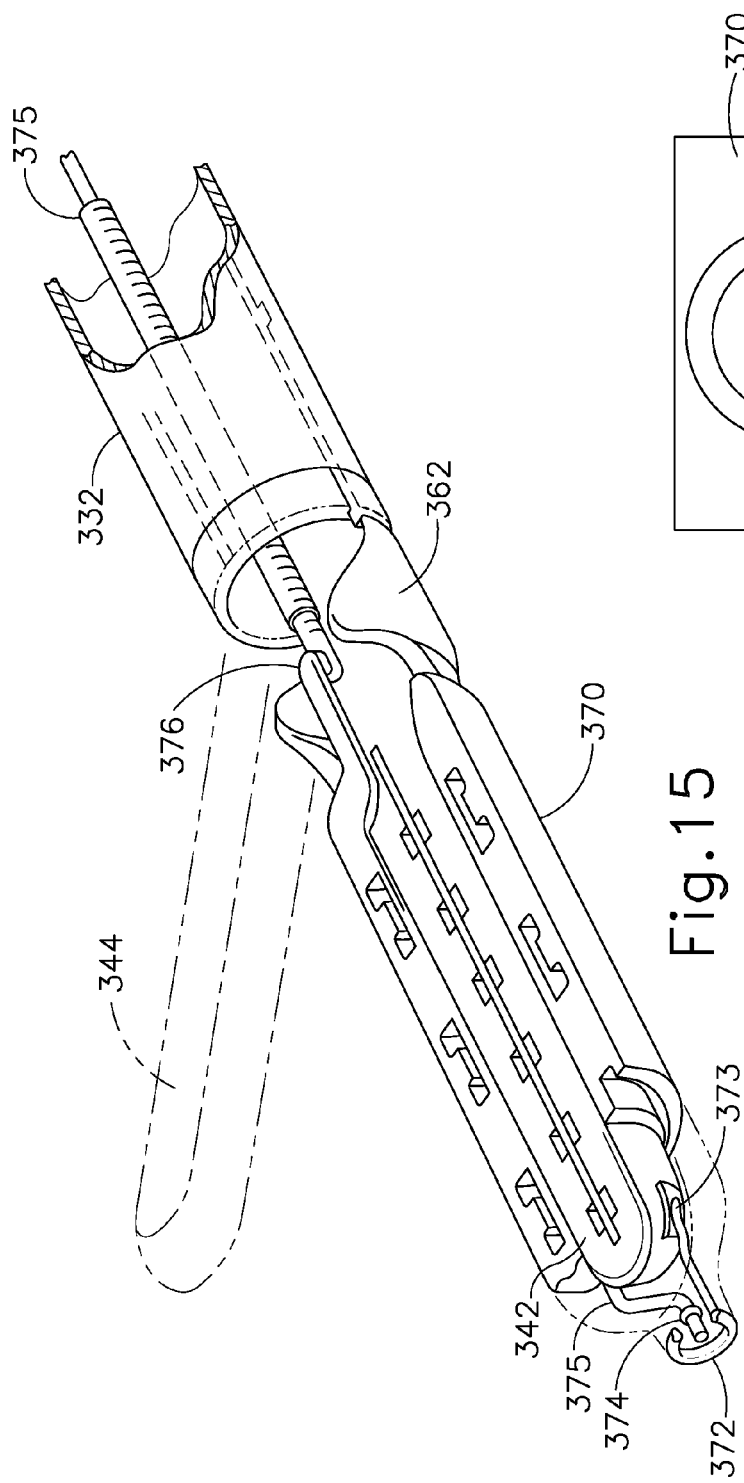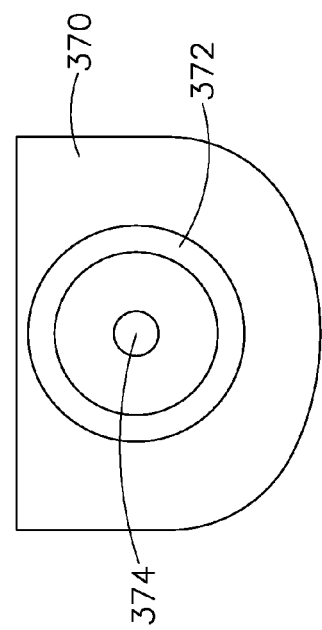
Fig.15
Fig.16

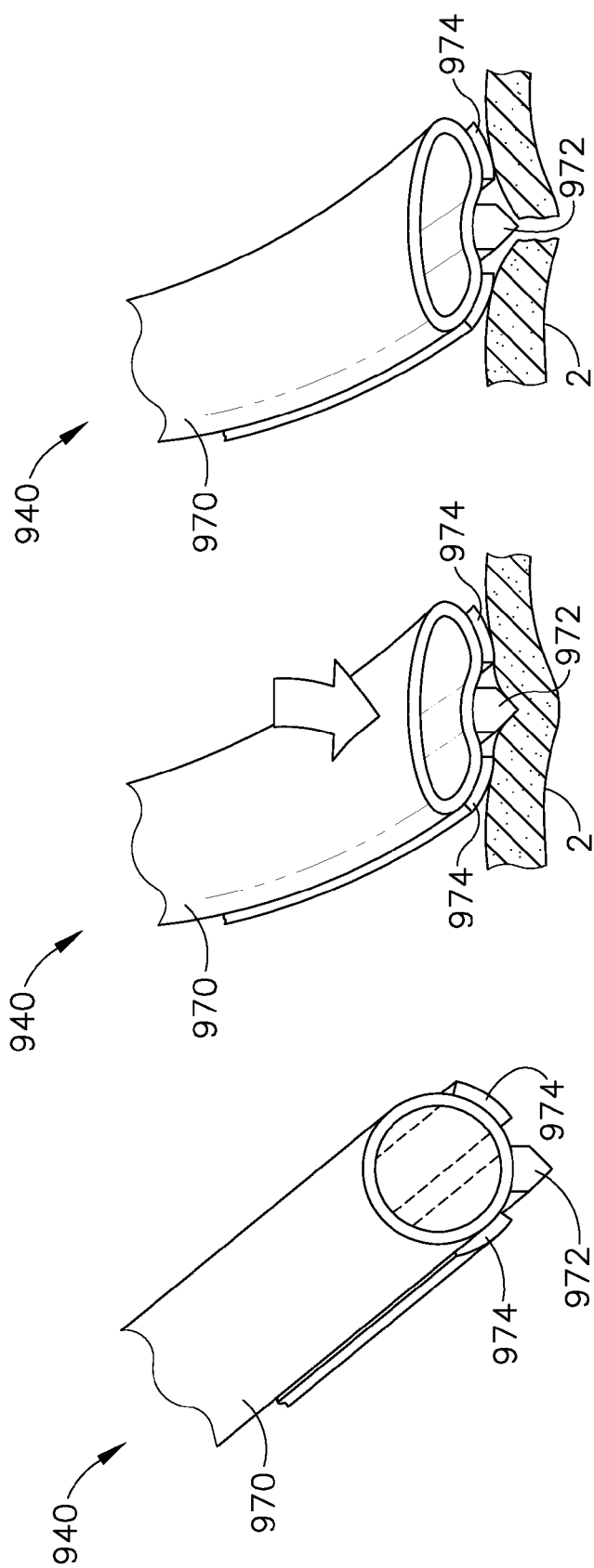

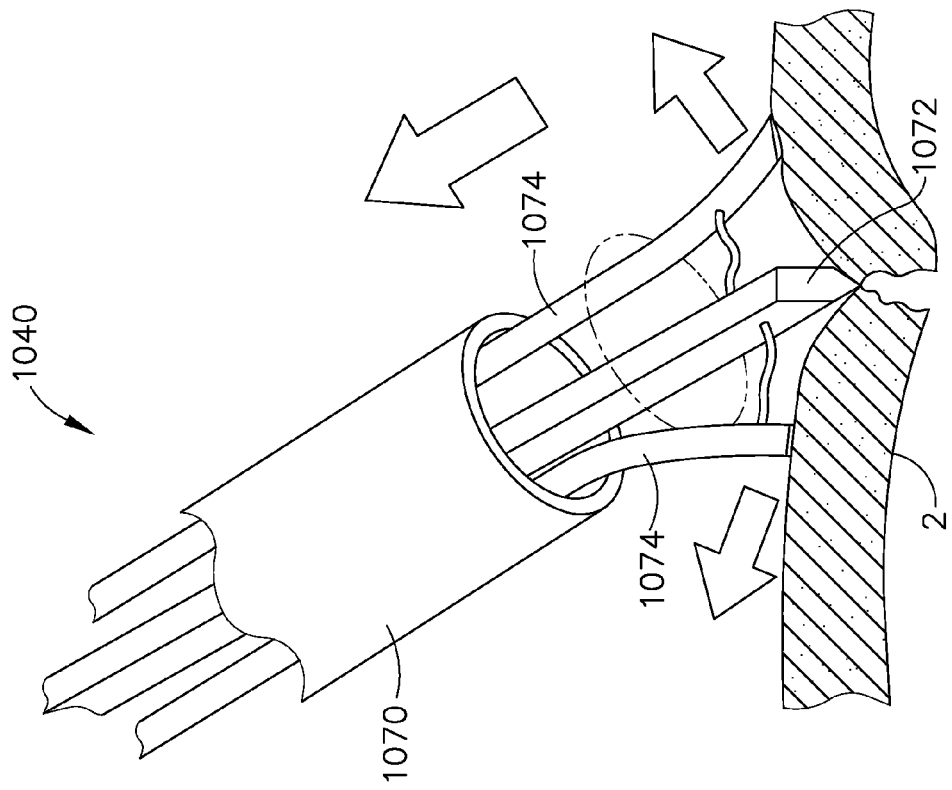
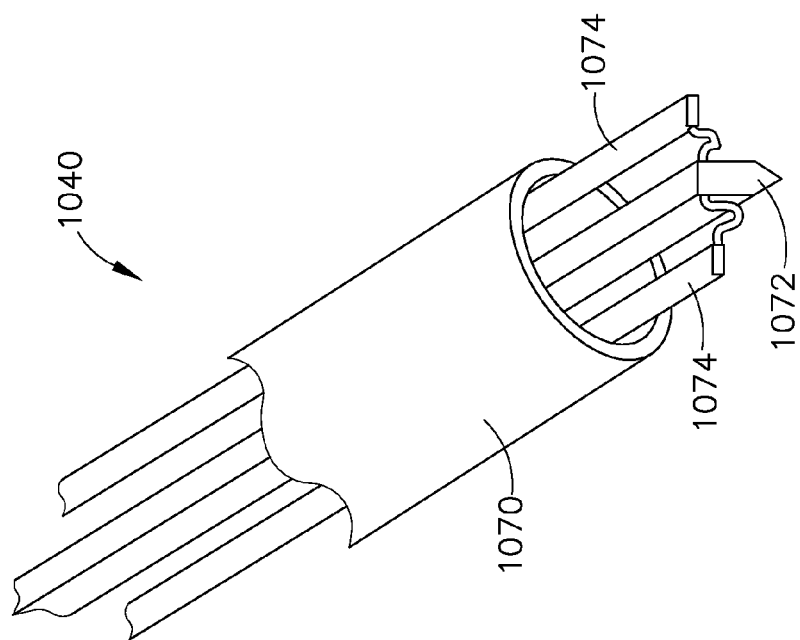

BIPOLAR ELECTROSURGICAL FEATURES FOR TARGETED HEMOSTASIS

BACKGROUND

A variety of surgical instruments include a tissue cutting element and one or more elements that transmit RF energy to tissue (e.g., to coagulate or seal the tissue). An example of such a device is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; U.S. Pub. No. 2012/0116379, entitled "Motor Driven Electrosurgical Device with Mechanical and Electrical Feedback," published May 10, 2012, now U.S. Pat. No. 9,161,803, issued Oct. 20, 2015, the disclosure of which is incorporated by reference herein; U.S. Pub. No. 2012/0078243, entitled "Control Features for Articulating Surgical Device," published Mar. 29, 2012, the disclosure of which is incorporated by reference herein; U.S. Pub. No. 2012/0078247, entitled "Articulation Joint Features for Articulating Surgical Device," published Mar. 29, 2012, now U.S. Pat. No. 9,402,682, issued Aug. 2, 2016, the disclosure of which is incorporated by reference herein; U.S. patent application Ser. No. 13/622,729, entitled "Surgical Instrument with Multi-Phase Trigger Bias," filed Sep. 19, 2012, now U.S. Pat. No. 9,089,327, issued Jul. 28, 2015 the disclosure of which is incorporated by reference herein; and U.S. patent application Ser. No. 13/622,735, entitled "Surgical Instrument with Contained Dual Helix Actuator Assembly," filed Sep. 19, 2012, now U.S. Pub. No. 2013/0023868, published Jan. 24, 2013, the disclosure of which is incorporated by reference herein.

While several medical devices have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 15 depicts a bottom, partial perspective view of the end effector of FIG. 14, with portions of the end effector omitted to show further details of the electrode cap;

FIG. 16 depicts an end view of the electrode cap of FIG. 14;

FIG. 27A depicts a perspective view of another exemplary end effector for use with the instrument of FIG. 1;

FIG. 27B depicts a perspective view of the end effector of FIG. 27A pressed against tissue;

FIG. 27C depicts a perspective view of the end effector of FIG. 27A cutting tissue;

FIG. 28A depicts a perspective view of another exemplary end effector for use with the instrument of FIG. 1;

FIG. 28B depicts a perspective view of the end effector of FIG. 28A cutting tissue;

Figure 1:
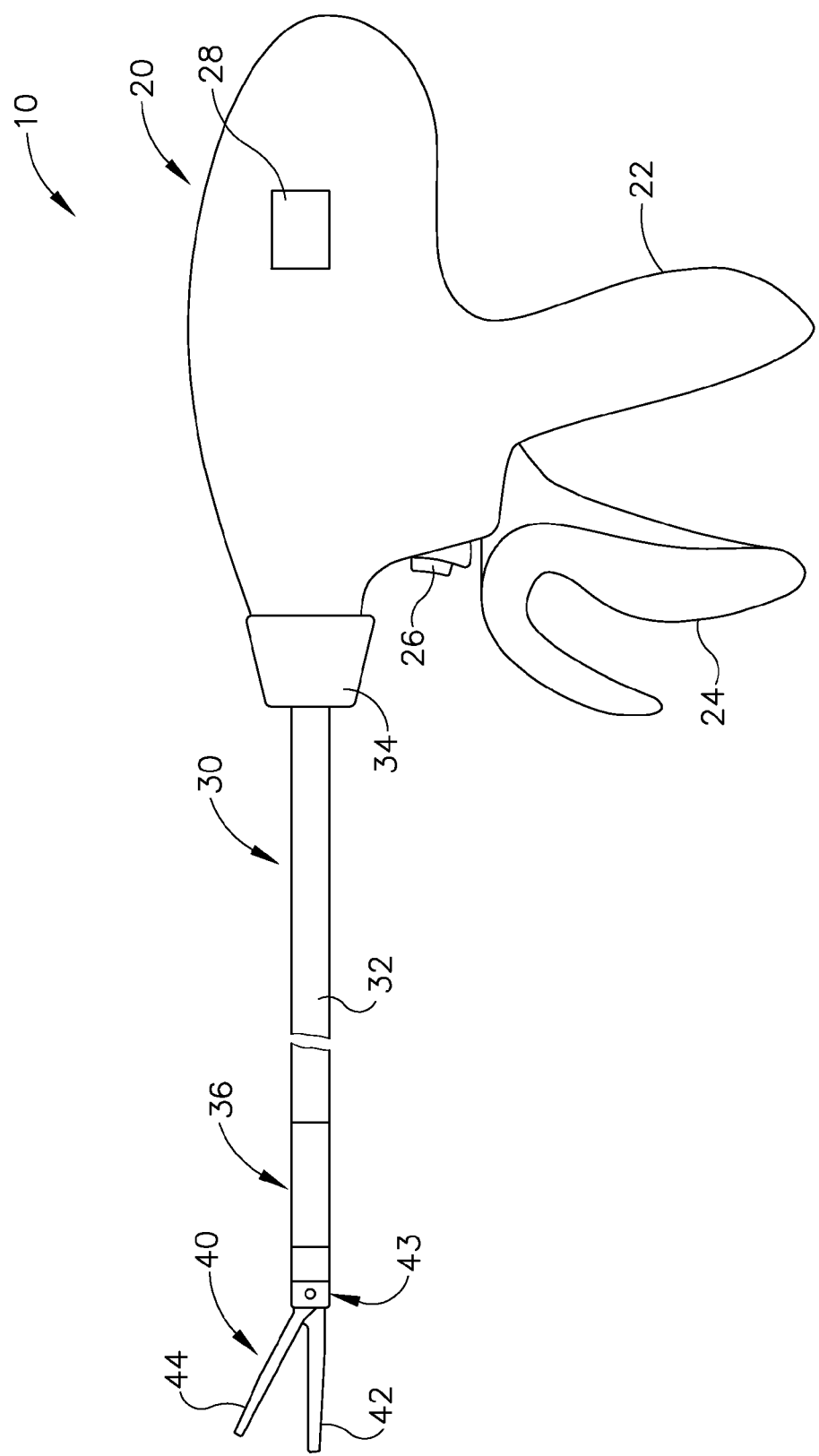
FIG. 1 depicts a side elevational view of an exemplary electrosurgical medical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Electrosurgical Device with Articulation Feature

FIGS. 1-4 show an exemplary electrosurgical instrument (10) that is constructed and operable in accordance with at least some of the teachings of U.S. Pat. Nos. 6,500,176; 7,112,201; 7,125,409; 7,169,146; 7,186,253; 7,189,233; 7,220,951; 7,309,849; 7,311,709; 7,354,440; 7,381,209; U.S. Pub. No. 2011/0087218; now U.S. Pat. No. 8,939,974, issued Jan. 27, 2015; U.S. Pub. No. 2012/0116379, now U.S. Pat. No. 9,161,803, issued Oct. 20, 2015; U.S. Pub. No. 2012/0078243; U.S. Pub. No. 2012/0078247; now U.S. Pat. No. 9,402,682, issued Aug. 2, 2016; U.S. patent application Ser. Nos. 13/622,729; now U.S. Pat. No. 9,089,327, issued Jul. 28, 2015; and/or 13/622,735, now U.S. Pub. No. 2013/0023868, published Jan. 24, 2013. As described therein and as will be described in greater detail below, electrosurgical instrument (10) is operable to cut tissue and seal or weld tissue (e.g., a blood vessel, etc.) substantially simultaneously. In other words, electrosurgical instrument (10) operates similar to an endocutter type of stapler, except that electrosurgical instrument (10) provides tissue welding through application of bipolar RF energy instead of providing lines of staples to join tissue. It should also be understood that electrosurgical instrument (10) may have various structural and functional similarities with the ENSEAL® Tissue Sealing Device by Ethicon Endo-Surgery, Inc., of Cincinnati, Ohio. Furthermore, electrosurgical instrument (10) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to electrosurgical instrument (10), there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Exemplary Handpiece and Shaft

Electrosurgical instrument (10) of the present example includes a handpiece (20), a shaft (30) extending distally from handpiece (20), and an end effector (40) disposed at a distal end of shaft (30). Handpiece (20) of the present example includes a pistol grip (22), a pivoting trigger (24), an activation button (26), and an articulation control (28). Trigger (24) is pivotable toward and away from pistol grip (22) to selectively actuate end effector (40) as will be described in greater detail below. Activation button (26) is operable to selectively activate RF circuitry that is in communication with end effector (40), as will also be described in greater detail below. In some versions, activation button (26) also serves as a mechanical lockout against trigger (24), such that trigger (24) cannot be fully actuated unless button (26) is being pressed simultaneously. Examples of how such a lockout may be provided are disclosed in one or more of the references cited herein. In addition or in the alternative, trigger (24) may serve as an electrical and/or mechanical lockout against button (26), such that button (26) cannot be effectively activated unless trigger (24) is being squeezed simultaneously. It should be understood that pistol grip (22), trigger (24), and button (26) may be modified, substituted, supplemented, etc. in any suitable way, and that the descriptions of such components herein are merely illustrative.

Shaft (30) of the present example includes an outer sheath (32) and an articulation section (36). Articulation section (36) is operable to selectively position end effector (40) at various angles relative to the longitudinal axis defined by sheath (32). Articulation section (36) of shaft (30) may take a variety of forms. By way of example only, articulation section (36) may be configured in accordance with one or more teachings of U.S. Pub. No. 2012/0078247, now U.S. Pat. No. 9,402,682, issued Aug. 2, 2016, the disclosure of which is incorporated by reference herein. As another merely illustrative example, articulation section (36) may be configured in accordance with one or more teachings of U.S. Pub. No. 2012/0078248, entitled "Articulation Joint Features for Articulating Surgical Device," published Mar. 29, 2012, now U.S. Pat. No. 9,220,559, issued Dec. 29, 2015, the disclosure of which is incorporated by reference herein. Various other suitable forms that articulation section (36) may take will be apparent to those of ordinary skill in the art in view of the teachings herein. It should also be understood that some versions of instrument (10) may simply lack articulation section (36).

In some versions, shaft (30) is also rotatable about the longitudinal axis defined by sheath (32), relative to handpiece (20), via a knob (34). Such rotation may provide rotation of end effector (40) and shaft (30) unitarily. In some other versions, knob (34) is operable to rotate end effector (40) without rotating any portion of shaft (30) that is proximal of articulation section (36). As another merely illustrative example, electrosurgical instrument (10) may include one rotation control that provides rotatability of shaft (30) and end effector (40) as a single unit; and another rotation control that provides rotatability of end effector (40) without rotating any portion of shaft (30) that is proximal of articulation section (36). Other suitable rotation schemes will be apparent to those of ordinary skill in the art in view of the teachings herein. Of course, rotatable features may simply be omitted if desired.

Articulation control (28) of the present example is operable to selectively control articulation section (36) of shaft (30), to thereby selectively position end effector (40) at various angles relative to the longitudinal axis defined by shaft (30). By way of example only, some merely illustrative forms that articulation control (28) and other components of handpiece (20) may take are disclosed in U.S. Pub. No. 2012/0078243, the disclosure of which is incorporated by reference herein; in U.S. Pub. No. 2012/0078244, entitled "Control Features for Articulating Surgical Device," published Mar. 29, 2012, the disclosure of which is incorporated by reference herein; and in U.S. patent application Ser. No. 13/622,735, now U.S. Pub. No. 2013/0023868, published Jan. 24, 2013, the disclosure of which is incorporated by reference herein. Still other suitable forms that articulation control (28) may take will be apparent to those of ordinary skill in the art in view of the teachings herein. It should also be understood that some versions of instrument (10) may simply lack an articulation control (28).

B. Exemplary End Effector

End effector (40) of the present example comprises a first jaw (42) and a second jaw (44). In the present example, second jaw (44) is substantially fixed relative to shaft (30); while first jaw (42) pivots relative to shaft (30), toward and away from second jaw (42). In some versions, actuators such as rods or cables, etc., may extend through sheath (32) and be joined with first jaw (42) at a pivotal coupling (43), such that longitudinal movement of the actuator rods/cables/etc. through shaft (30) provides pivoting of first jaw (42) relative to shaft (30) and relative to second jaw (44). Of course, jaws (42, 44) may instead have any other suitable kind of movement and may be actuated in any other suitable fashion. By way of example only, and as will be described in greater detail below, jaws (42, 44) may be actuated and thus closed by longitudinal translation of a firing beam (60), such that actuator rods/cables/etc. may simply be eliminated in some versions.

Figure 2:
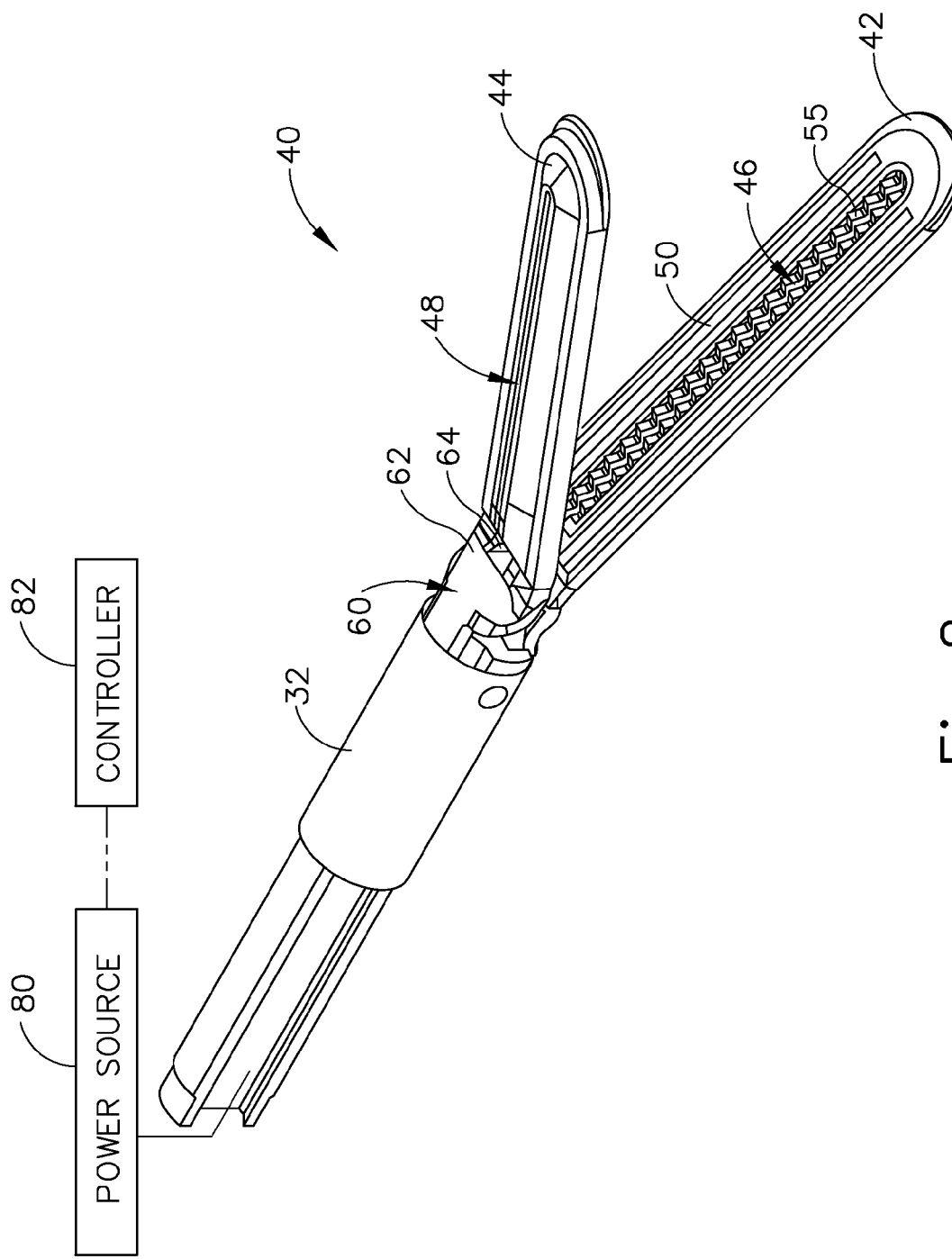
FIG. 2 depicts a perspective view of the end effector of the instrument of FIG. 1, in an open configuration.
Figure 3:
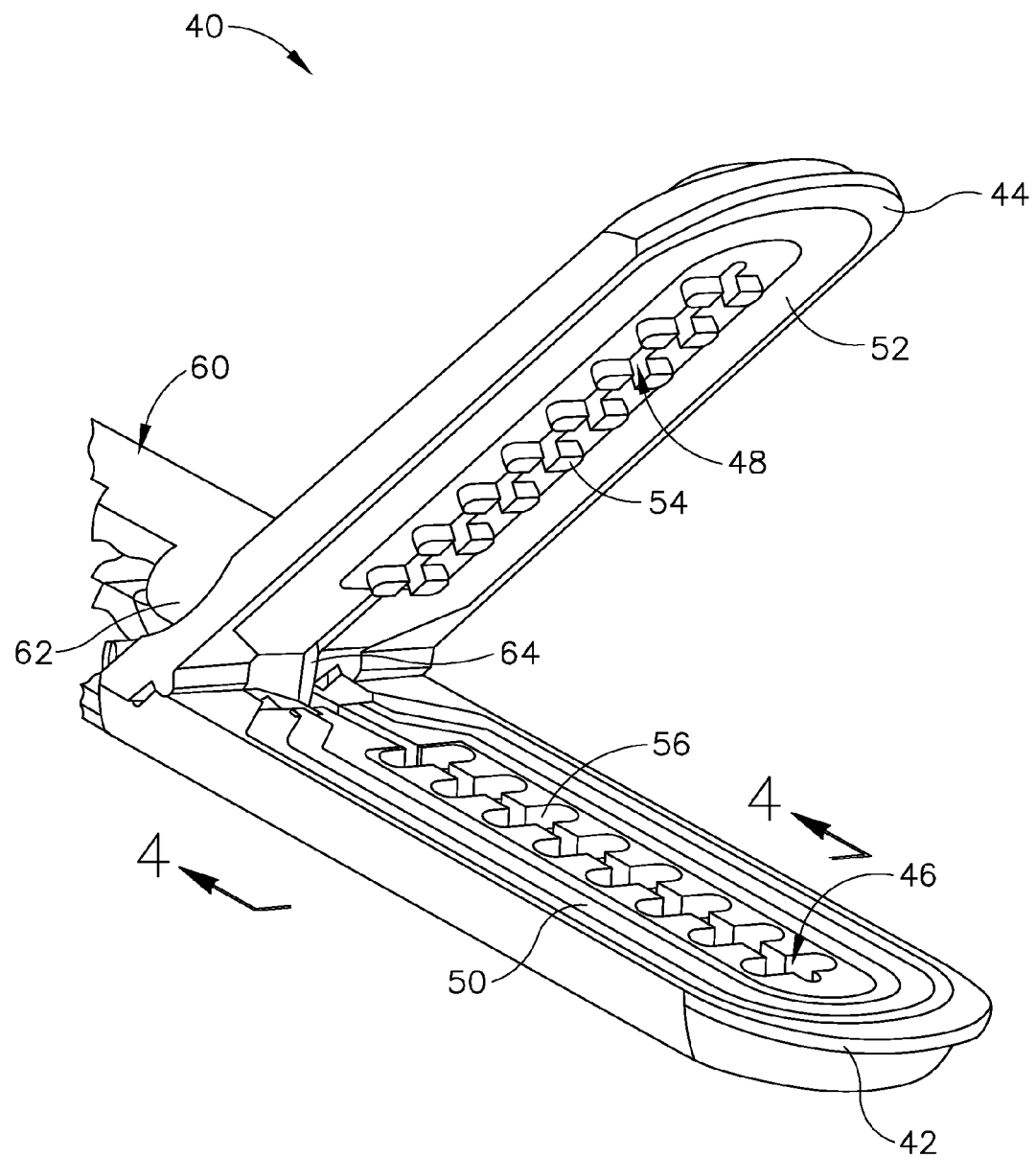
FIG. 3 depicts another perspective view of the end effector of the instrument of FIG. 1, in an open configuration.
Figure 4:
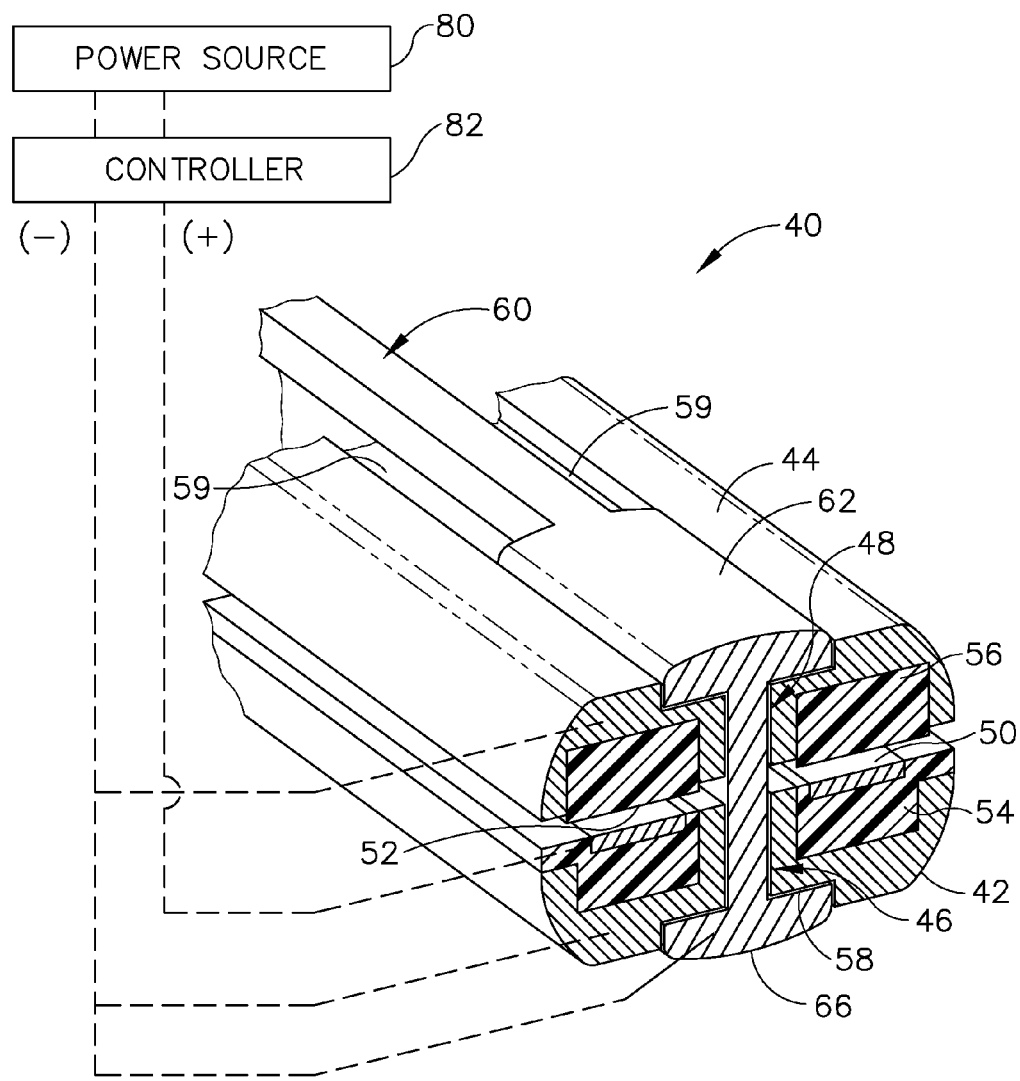
FIG. 4 depicts a cross-sectional end view of the end effector of FIG. 2, in a closed configuration and with the blade in a distal position.

As best seen in FIGS. 2-4, first jaw (42) defines a longitudinally extending elongate slot (46); while second jaw (44) also defines a longitudinally extending elongate slot (48). In addition, the top side of first jaw (42) presents a first electrode surface (50); while the underside of second jaw (44) presents a second electrode surface (52). Electrode surfaces (50, 52) are in communication with an electrical source (80) via one or more conductors (not shown) that extend along the length of shaft (30). Electrical source (80) is operable to deliver RF energy to first electrode surface (50) at a first polarity and to second electrode surface (52) at a second (opposite) polarity, such that RF current flows between electrode surfaces (50, 52) and thereby through tissue captured between jaws (42, 44). In some versions, firing beam (60) serves as an electrical conductor that cooperates with electrode surfaces (50, 52) (e.g., as a ground return) for delivery of bipolar RF energy captured between jaws (42, 44). Electrical source (80) may be external to electrosurgical instrument (10) or may be integral with electrosurgical instrument (10) (e.g., in handpiece (20), etc.), as described in one or more references cited herein or otherwise. A controller (82) regulates delivery of power from electrical source (80) to electrode surfaces (50, 52). Controller (82) may also be external to electrosurgical instrument (10) or may be integral with electrosurgical instrument (10) (e.g., in handpiece (20), etc.), as described in one or more references cited herein or otherwise. It should also be understood that electrode surfaces (50, 52) may be provided in a variety of alternative locations, configurations, and relationships.

As best seen in FIG. 4, the lower side of first jaw (42) includes a longitudinally extending recess (58) adjacent to slot (46); while the upper side of second jaw (44) includes a longitudinally extending recess (59) adjacent to slot (48). FIG. 2 shows the upper side of first jaw (42) including a plurality of teeth serrations (46). It should be understood that the lower side of second jaw (44) may include complementary serrations that nest with serrations (46), to enhance gripping of tissue captured between jaws (42, 44) without necessarily tearing the tissue. FIG. 3 shows an example of serrations (46) in first jaw (42) as mainly recesses; with serrations (48) in second jaw (44) as mainly protrusions. Of course, serrations (46, 48) may take any other suitable form or may be simply omitted altogether. It should also be understood that serrations (46, 48) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (42, 44).

With jaws (42, 44) in a closed position, shaft (30) and end effector (40) are sized and configured to fit through trocars having various inner diameters, such that electrosurgical instrument (10) is usable in minimally invasive surgery, though of course electrosurgical instrument (10) could also be used in open procedures if desired. By way of example only, with jaws (42, 44) in a closed position, shaft (30) and end effector (40) may present an outer diameter of approximately 5 mm. Alternatively, shaft (30) and end effector (40) may present any other suitable outer diameter (e.g., between approximately 2 mm and approximately 20 mm, etc.).

As another merely illustrative variation, either jaw (42, 44) or both of jaws (42, 44) may include at least one port, passageway, conduit, and/or other feature that is operable to draw steam, smoke, and/or other gases/vapors/etc. from the surgical site. Such a feature may be in communication with a source of suction, such as an external source or a source within handpiece (20), etc. In addition, end effector (40) may include one or more tissue cooling features (not shown) that reduce the degree or extent of thermal spread caused by end effector (40) on adjacent tissue when electrode surfaces (50, 52) are activated. Various suitable forms that such cooling features may take will be apparent to those of ordinary skill in the art in view of the teachings herein.

In some versions, end effector (40) includes one or more sensors (not shown) that are configured to sense a variety of parameters at end effector (40), including but not limited to temperature of adjacent tissue, electrical resistance or impedance of adjacent tissue, voltage across adjacent tissue, forces exerted on jaws (42, 44) by adjacent tissue, etc. By way of example only, end effector (40) may include one or more positive temperature coefficient (PTC) thermistor bodies (54, 56) (e.g., PTC polymer, etc.), located adjacent to electrodes (50, 52) and/or elsewhere. Data from sensors may be communicated to controller (82). Controller (82) may process such data in a variety of ways. By way of example only, controller (82) may modulate or otherwise change the RF energy being delivered to electrode surfaces (50, 52), based at least in part on data acquired from one or more sensors at end effector (40). In addition or in the alternative, controller (82) may alert the user to one or more conditions via an audio and/or visual feedback device (e.g., speaker, lights, display screen, etc.), based at least in part on data acquired from one or more sensors at end effector (40). It should also be understood that some kinds of sensors need not necessarily be in communication with controller (82), and may simply provide a purely localized effect at end effector (40). For instance, a PTC thermistor bodies (54, 56) at end effector (40) may automatically reduce the energy delivery at electrode surfaces (50, 52) as the temperature of the tissue and/or end effector (40) increases, thereby reducing the likelihood of overheating. In some such versions, a PTC thermistor element is in series with power source (80) and electrode surface (50, 52); and the PTC thermistor provides an increased impedance (reducing flow of current) in response to temperatures exceeding a threshold. Furthermore, it should be understood that electrode surfaces (50, 52) may be used as sensors (e.g., to sense tissue impedance, etc.). Various kinds of sensors that may be incorporated into electrosurgical instrument (10) will be apparent to those of ordinary skill in the art in view of the teachings herein. Similarly various things that can be done with data from sensors, by controller (82) or otherwise, will be apparent to those of ordinary skill in the art in view of the teachings herein. Other suitable variations for end effector (40) will also be apparent to those of ordinary skill in the art in view of the teachings herein.

C. Exemplary Firing Beam

As also seen in FIGS. 2-4, electrosurgical instrument (10) of the present example includes a firing beam (60) that is longitudinally movable along part of the length of end effector (40). Firing beam (60) is coaxially positioned within shaft (30), extends along the length of shaft (30), and translates longitudinally within shaft (30) (including articulation section (36) in the present example), though it should be understood that firing beam (60) and shaft (30) may have any other suitable relationship. Firing beam (60) includes a sharp distal blade (64), an upper flange (62), and a lower flange (66). As best seen in FIG. 4, distal blade (64) extends through slots (46, 48) of jaws (42, 44), with upper flange (62) being located above jaw (44) in recess (59) and lower flange (66) being located below jaw (42) in recess (58). The configuration of distal blade (64) and flanges (62, 66) provides an "I-beam" type of cross section at the distal end of firing beam (60). While flanges (62, 66) extend longitudinally only along a small portion of the length of firing beam (60) in the present example, it should be understood that flanges (62, 66) may extend longitudinally along any suitable length of firing beam (60). In addition, while flanges (62, 66) are positioned along the exterior of jaws (42, 44), flanges (62, 66) may alternatively be disposed in corresponding slots formed within jaws (42, 44). For instance, each jaw (42, 44) may define a "T"-shaped slot, with parts of distal blade (64) being disposed in one vertical portion of each "T"-shaped slot and with flanges (62, 66) being disposed in the horizontal portions of the "T"-shaped slots. Various other suitable configurations and relationships will be apparent to those of ordinary skill in the art in view of the teachings herein.

Distal blade (64) is substantially sharp, such that distal blade (64) will readily sever tissue that is captured between jaws (42, 44). Distal blade (64) is also electrically grounded in the present example, providing a return path for RF energy as described elsewhere herein. In some other versions, distal blade (64) serves as an active electrode. In addition or in the alternative, distal blade (64) may be selectively energized with ultrasonic energy (e.g., harmonic vibrations at approximately 55.5 kHz, etc.).

The "I-beam" type of configuration of firing beam (60) provides closure of jaws (42, 44) as firing beam (60) is advanced distally. In particular, flange (62) urges jaw (44) pivotally toward jaw (42) as firing beam (60) is advanced from a proximal position (FIGS. 1-3) to a distal position (FIG. 4), by bearing against recess (59) formed in jaw (44). This closing effect on jaws (42, 44) by firing beam (60) may occur before distal blade (64) reaches tissue captured between jaws (42, 44). Such staging of encounters by firing beam (60) may reduce the force required to squeeze grip (24) to actuate firing beam (60) through a full firing stroke. In other words, in some such versions, firing beam (60) may have already overcome an initial resistance required to substantially close jaws (42, 44) on tissue before encountering resistance from severing the tissue captured between jaws (42, 44). Of course, any other suitable staging may be provided.

In the present example, flange (62) is configured to cam against a ramp feature at the proximal end of jaw (44) to open jaw (42) when firing beam (60) is retracted to a proximal position and to hold jaw (42) open when firing beam (60) remains at the proximal position. This camming capability may facilitate use of end effector (40) to separate layers of tissue, to perform blunt dissections, etc., by forcing jaws (42, 44) apart from a closed position. In some other versions, jaws (42, 44) are resiliently biased to an open position by a spring or other type of resilient feature. While jaws (42, 44) close or open as firing beam (60) is translated in the present example, it should be understood that other versions may provide independent movement of jaws (42, 44) and firing beam (60). By way of example only, one or more cables, rods, beams, or other features may extend through shaft (30) to selectively actuate jaws (42, 44) independently of firing beam (60). Such jaw (42, 44) actuation features may be separately controlled by a dedicated feature of handpiece (20). Alternatively, such jaw actuation features may be controlled by trigger (24) in addition to having trigger (24) control firing beam (60). It should also be understood that firing beam (60) may be resiliently biased to a proximal position, such that firing beam (60) retracts proximally when a user relaxes their grip on trigger (24).

D. Exemplary Operation

In an exemplary use, end effector (40) is inserted into a patient via a trocar. Articulation section (36) is substantially straight when end effector (40) and part of shaft (30) are inserted through the trocar. Articulation control (28) may then be manipulated to pivot or flex articulation section (36) of shaft (30) in order to position end effector (40) at a desired position and orientation relative to an anatomical structure within the patient. Two layers of tissue of the anatomical structure are then captured between jaws (42, 44) by squeezing trigger (24) toward pistol grip (22). Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (10) is perpendicular to the longitudinal axis defined by end effector (40), etc.). In other words, the lengths of jaws (42, 44) may be oriented perpendicular to (or at least generally transverse to) the length of the blood vessel. As noted above, flanges (62, 66) cammingly act to pivot jaw (42) toward jaw (44) when firing beam (60) is actuated distally by squeezing trigger (24) toward pistol grip (22). Jaws (42, 44) may be substantially clamping tissue before trigger (24) has swept through a full range of motion toward pistol grip (22), such that trigger (24) may continue pivoting toward pistol grip (22) through a subsequent range of motion after jaws (42, 44) have substantially clamped on the tissue.

With tissue layers captured between jaws (42, 44) firing beam (60) continues to advance distally by the user squeezing trigger (24) further toward pistol grip (22). As firing beam (60) continues to advance distally, distal blade (64) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (62, 66) immediately above and below jaws (42, 44), respectively, may help keep jaws (42, 44) in a closed and tightly clamping position. In particular, flanges (62, 66) may help maintain a significantly compressive force between jaws (42, 44). With severed tissue layer portions being compressed between jaws (42, 44), electrode surfaces (50, 52) are activated with bipolar RF energy by the user depressing activation button (26). In some versions, electrodes (50, 52) are selectively coupled with power source (80) (e.g., by the user depressing button (26), etc.) such that electrode surfaces (50, 52) of jaws (42, 44) are activated with a common first polarity while firing beam (60) is activated at a second polarity that is opposite to the first polarity. Thus, a bipolar RF current flows between firing beam (60) and electrode surfaces (50, 52) of jaws (42, 44), through the compressed regions of severed tissue layer portions. In some other versions, electrode surface (50) has one polarity while electrode surface (52) and firing beam (60) both have the other polarity. In either version (among at least some others), bipolar RF energy delivered by power source (80) ultimately electrosurgically welds the tissue layer portions on one side of firing beam (60) together and the tissue layer portions on the other side of firing beam (60) together.

In certain circumstances, the heat generated by activated electrode surfaces (50, 52) can denature the collagen within the tissue layer portions and, in cooperation with clamping pressure provided by jaws (42, 44), the denatured collagen can form a seal within the tissue layer portions. Thus, the severed ends of the natural lumen defining anatomical structure are hemostatically sealed shut, such that the severed ends will not leak bodily fluids. In some versions, electrode surfaces (50, 52) may be activated with bipolar RF energy before firing beam (60) even begins to translate distally and thus before the tissue is even severed. For instance, such timing may be provided in versions where button (26) serves as a mechanical lockout relative to trigger (24) in addition to serving as a switch between power source (80) and electrode surfaces (50, 52). Other suitable ways in which instrument (10) may be operable and operated will be apparent to those of ordinary skill in the art in view of the teachings herein.

II. Exemplary Bipolar Electrosurgical Features

In some instances, when instrument (10) is used to cut and seal tissue, some portions of tissue at the surgical site may bleed after end effector (40) is pulled away from the transected/sealed tissue. These tissue areas may be at or near the tissue weld site. It may be desirable to provide additional electrodes at end effector (40) to enable the surgeon to "touch up" these bleeding tissue areas by using RF energy to further seal the bleeding tissue in a highly localized fashion, without having to place such tissue between jaws (42, 44) of end effector (40). As described in greater detail below, this may be accomplished using electrodes that are outside the clamping regions of jaws (42, 44), with such electrodes being exposed even when jaws (42, 44) are closed together. In versions where end effector (40) is configured to transmit bipolar RF energy, these external electrodes may need to be configured and positioned such that the bleeding tissue can be readily placed between electrodes in a pair, to enable the RF energy to pass through the tissue from one electrode to the other electrode. It may also be necessary in some instances for the surgeon to apply pressure to the tissue with the electrodes in order for the tissue to be properly sealed by the bipolar electrodes. Several examples of these types of bipolar RF "bleeder touch up" features are described in greater detail below, while other examples will be apparent to those of ordinary skill in the art in view of the teachings herein.

It should be understood that any of the following "bleeder touch up" features may be readily incorporated into end effector (40) of instrument (10). For instance, such features may be integrated directly into one or both of jaws (42, 44). Alternatively, such features may be provided as a cartridge, adapter, or other type of retrofit that couples with end effector (40). As yet another merely illustrative alternative, such features may be provided as separate, stand-alone instruments; or may be incorporated into various other kinds of surgical instruments.

By way of example only, while examples herein are described mainly in the context of an RF electrosurgical device, it should be understood that any of the features described below may be readily incorporated into numerous kinds of harmonic surgical instruments that include an ultrasonic blade or other ultrasonic feature. For instance, some ultrasonic surgical instruments include a pivoting clamp arm that may receive features like those described below (e.g., on the back of the clamp arm and/or on the distal tip of the clamp arm, etc.). Such combinations may thus provide a surgical device that is a hybrid of an ultrasonic surgical device and an RF electrosurgical device. Examples of ultrasonic devices that the below teachings may be readily combined with are disclosed in U.S. Pat. Pub. No. 2006/0079874, entitled "Tissue Pad for Use with an Ultrasonic Surgical Instrument," published Apr. 13, 2006, the disclosure of which is incorporated by reference herein; U.S. Pat. Pub. No. 2007/0191713, entitled "Ultrasonic Device for Cutting and Coagulating," published Aug. 16, 2007, the disclosure of which is incorporated by reference herein; U.S. Pat. Pub. No. 2007/0282333, entitled "Ultrasonic Waveguide and Blade," published Dec. 6, 2007, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pat. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; and U.S. Pat. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein. Other suitable combinations will be apparent to those of ordinary skill in the art in view of the teachings herein.

A. Exemplary Electrode Cap

Figure 5A:
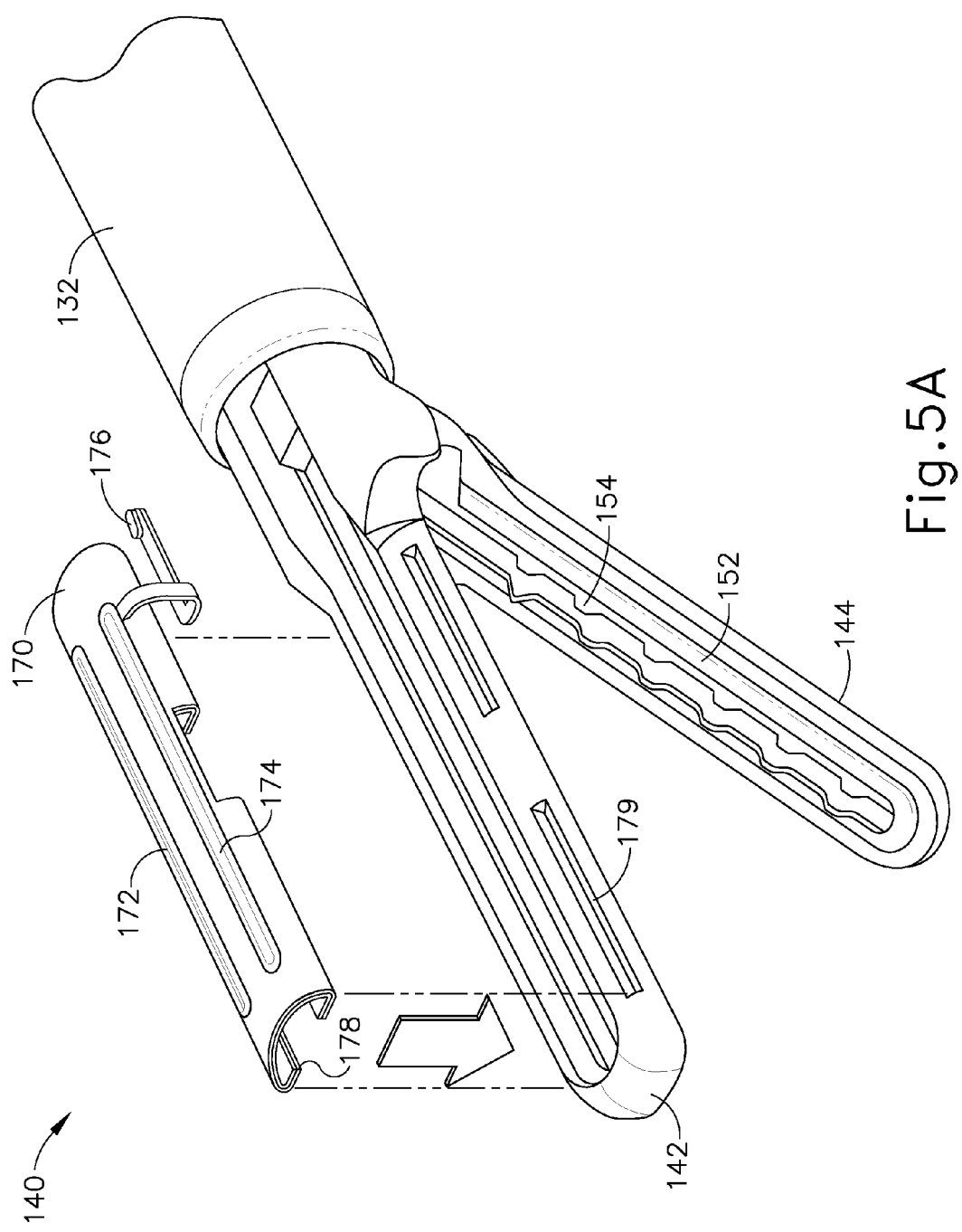
FIG. 5A depicts a top perspective view of another exemplary end effector for use with the instrument of FIG. 1, in an open position showing an electrode cap.

FIGS. 5A-12 show an exemplary electrode cap (170) for coupling with an end effector (140). End effector (140) is similar to end effector (40), except that end effector (140) comprises engagement recesses (179) positioned on the exterior of the side wall of stationary jaw (142), as shown in FIG. 5A. Electrode cap (170) is sized to couple to the exterior surface of stationary jaw (142). This allows any electrode wiring to cap (170) to remain stationary while pivoting jaw (144) pivots relative to stationary jaw (142). Cap (170) comprises protrusions (178), electrode surfaces (172, 174), and an electrode coupling feature (176). Protrusions (178) extend from cap (170) to correspond to engagement recesses (179). Cap (170) may be positioned over jaw (142) and pressed onto jaw (142), as shown in FIG. 5B. Protrusions (178) may flex outward when cap (170) is being pressed onto jaw (142). Protrusions (178) then flex inward and insert into engagement recesses (179) to secure cap (170) to jaw (142) with a snap fit. Electrode surfaces (172, 174) are positioned on the exterior surface of cap (170). First electrode surface (172) is configured at a first polarity and second electrode surface (174) is configured at a second (opposite) polarity, such that RF current flows through any conductive material (e.g. tissue) that is placed between electrode surfaces (172, 174).

Figure 5B:
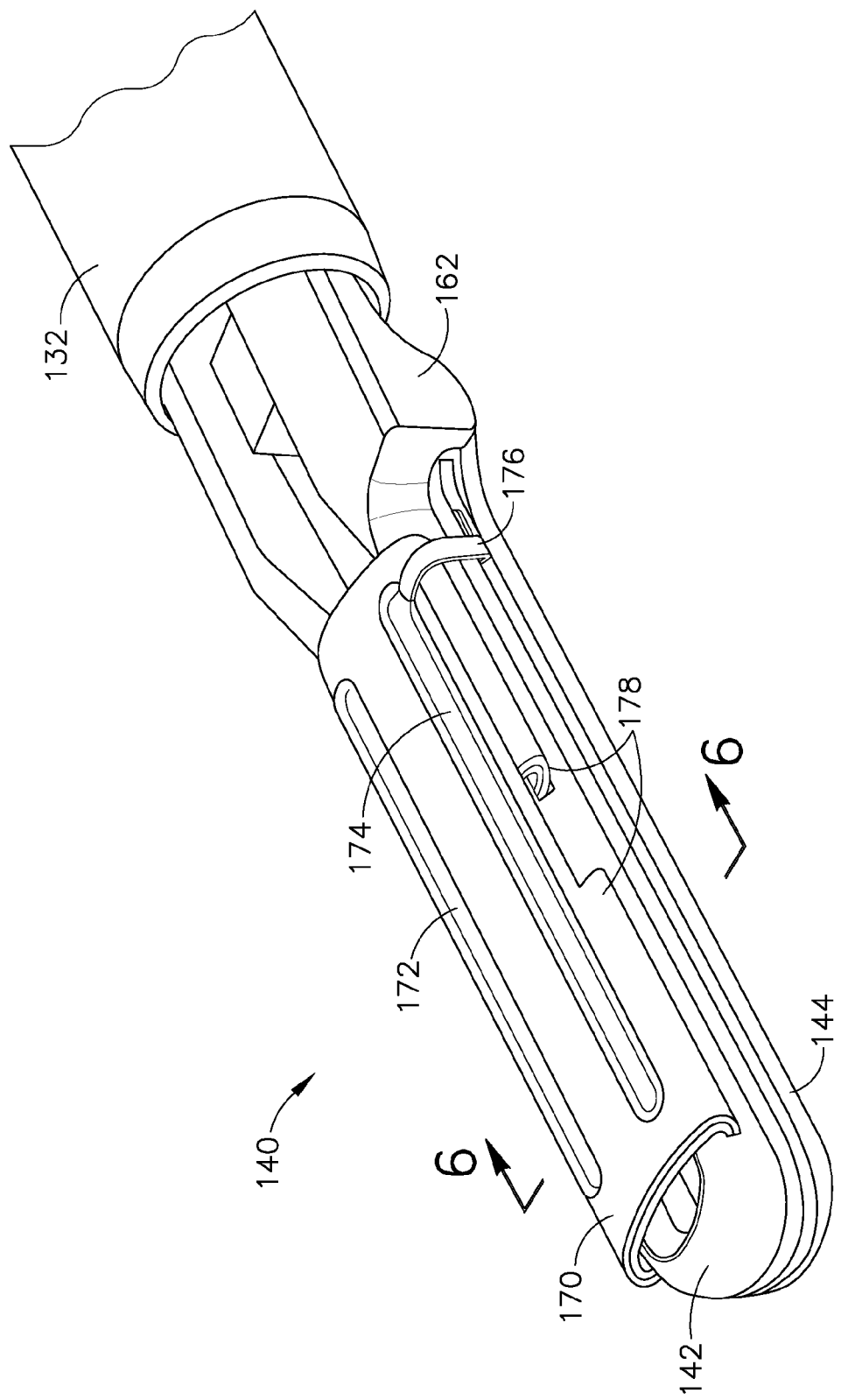
FIG. 5B depicts a top perspective view of the end effector of FIG. 5A, in a closed configuration coupled with the electrode cap.
Figure 6:
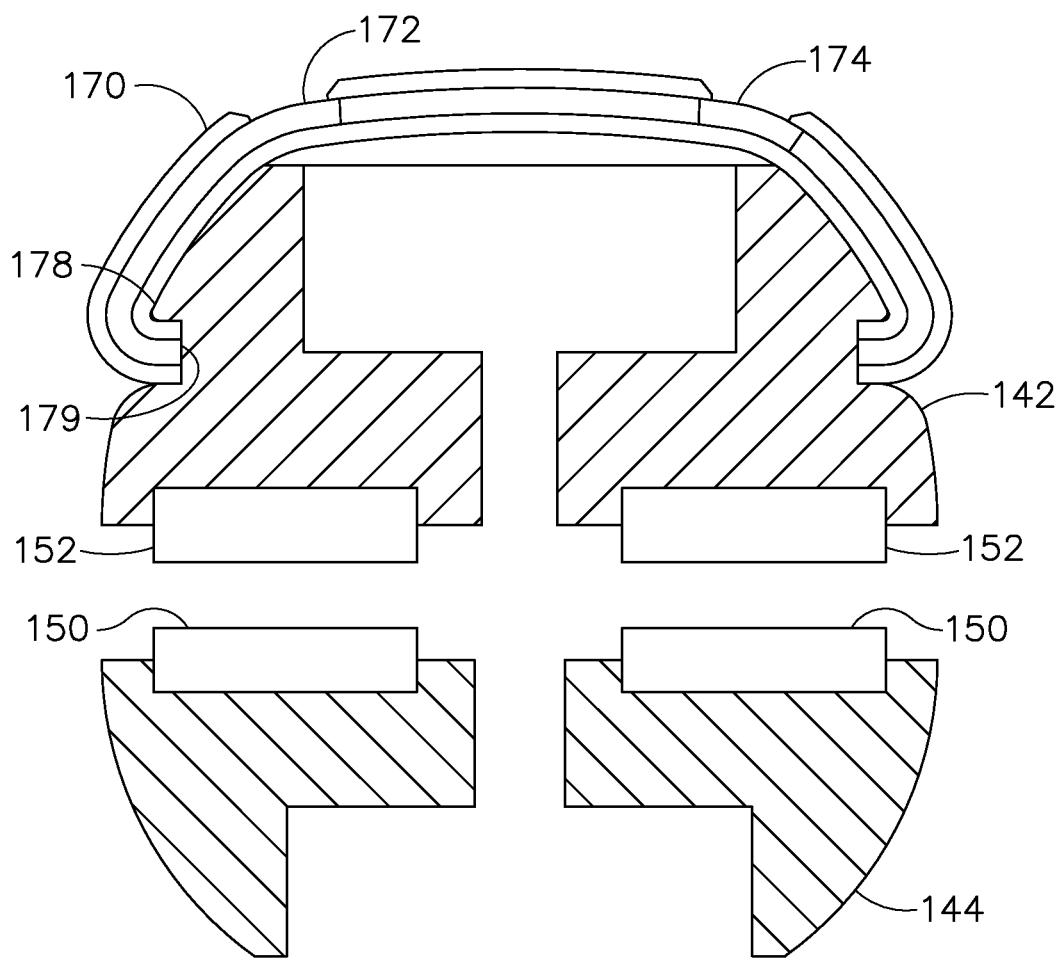
FIG. 6 depicts a cross-sectional end view of the end effector of FIG. 5B.
Figure 7:
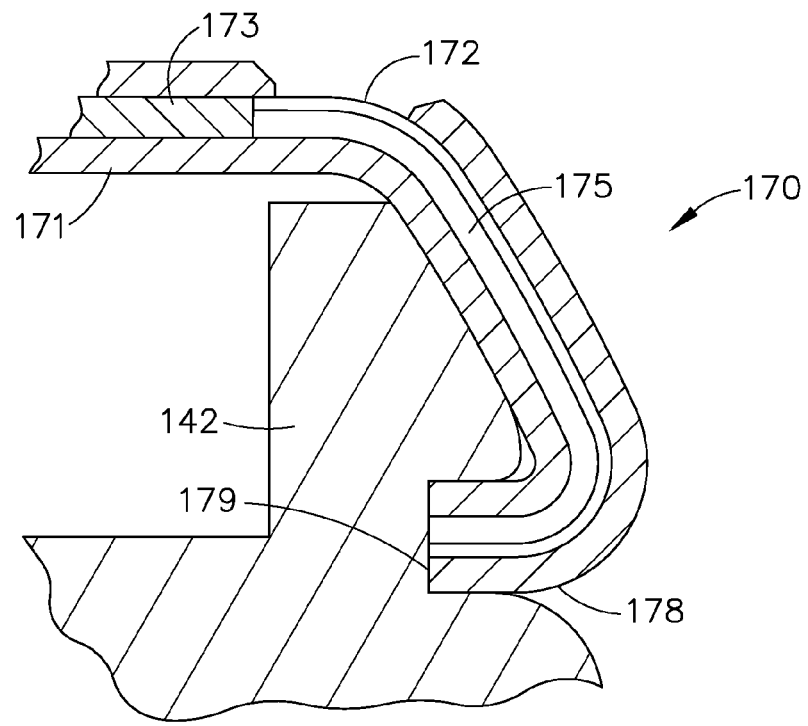
FIG. 7 depicts a partial cross-sectional view of the end effector of FIG. 6.
Figure 8:
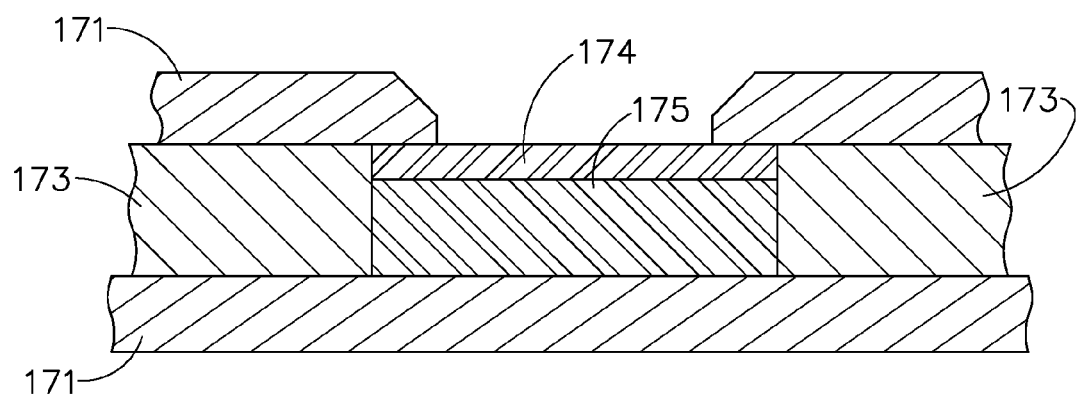
FIG. 8 depicts a partial cross-sectional view of the electrode cap of FIG. 7.

As shown in FIG. 5B, electrode surface (174) is configured to receive RF energy through electrode coupling feature (176). Electrode coupling feature (176) is configured to wrap around a portion of jaw (142) to contact the RF energy supplied to electrode surface (150) of jaw (144). As shown in FIG. 8, a plastic filler (173) or some other insulator is positioned on either side of electrode surface (174) to insulate electrode surface (174) from the RF energy being applied to jaw (142). As shown in FIGS. 6-7, electrode surface (172) is configured to receive RF energy through direct contact with jaw (142). Electrode surface (172) wraps around a portion of jaw (142) to directly contact jaw (142) to receive RF energy supplied to electrode surface (152) of jaw (142). Electrode surface (172) contacts jaw (142) where protrusion (178) of cap (170) is coupled to engagement recess (179) of jaw (142). Alternatively, each electrode surface (172, 174) may have its own electrode coupling feature (176) to couple to end effector (140) at different polarities. In some versions, electrode surfaces (172, 174) receive RF energy whenever electrodes (150, 152) of jaws (142, 144) receive RF energy. In some other versions, electrode surfaces (172, 174) receive RF energy independently relative to electrodes (150, 152) of jaws (142, 144). This may vary based on the configuration of electrode coupling feature (176), etc.

Both electrode surfaces (172, 174) of cap (170) are positioned vertically between layers of an insulated plastic film (171), as shown in FIGS. 7-8. The lower layer of plastic film (171) extends around the lower surface of cap (170) to insulate cap (170) from jaw (142). The upper layer of plastic film (171) comprises an opening to expose electrode surfaces (172, 174). Electrode surfaces (172, 174) may be formed from a conductive material laminate, such as titanium, aluminum, or copper, etc. Electrode surfaces (172, 174) may be formed from a single material, or a layering of multiple materials. Other suitable materials will be apparent to one with ordinary skill in the art in view of the teachings herein. While electrode surfaces (172, 174) are shown as direct contact metal electrodes to receive RF energy either through electrode coupling feature (176) or jaw (142), inductive coupling may also be used such that electrode surfaces (172, 174) receive RF energy from instrument (10) via inductive coupling. Because electrode surfaces (172, 174) may become dirty, electrode surfaces (172, 174) may be greased or coated with a biocompatible dielectric grease or coating to help minimize any degradation in performance.

Figure 9:
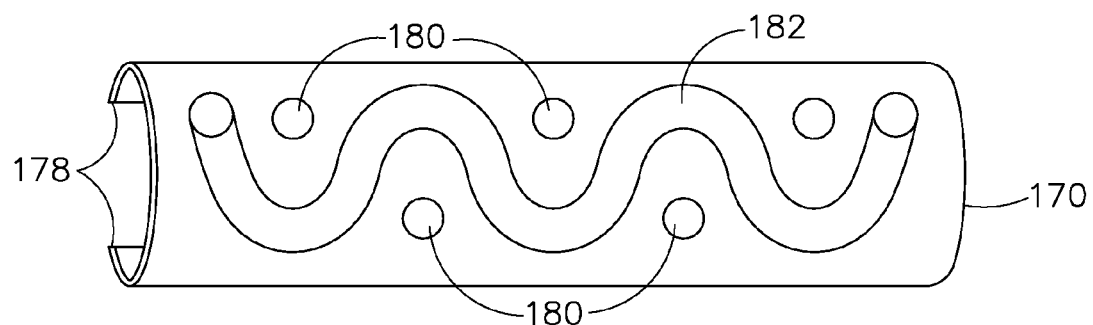
FIG. 9 depicts a top view of the electrode cap of FIG. 5A showing another exemplary electrode configuration.
Figure 10:
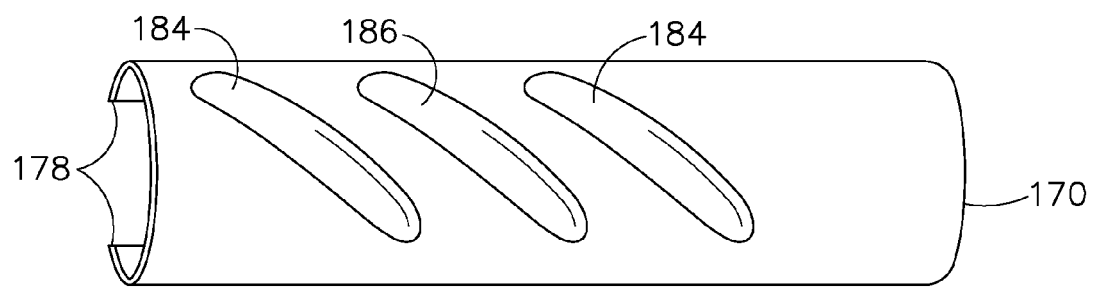
FIG. 10 depicts a top view of the electrode cap of FIG. 5A showing another exemplary electrode configuration.
Figure 11:
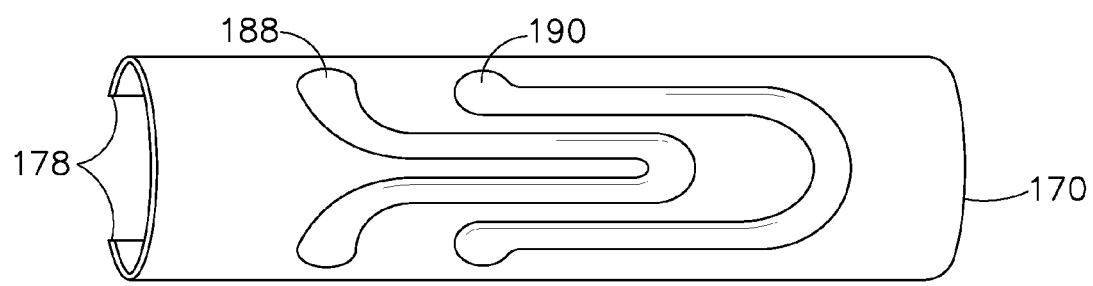
FIG. 11 depicts a top view of the electrode cap of FIG. 5A showing another exemplary electrode configuration.

Electrode surfaces (172, 174) may have multiple configurations. In the present example, electrode surfaces (172, 174) extend substantially in a line along cap (170). Alternative configurations are shown in FIGS. 9-11. In FIG. 9, a first electrode surface (182) with a first polarity extends along cap (170) in a waved pattern. Second electrode surfaces (180) with a second, opposite polarity are configured as dots positioned between the waved pattern of first electrode surface (182). In FIG. 10, first electrode surfaces (184) with a first polarity are positioned obliquely across cap (170). A second electrode surface (186) with a second, opposite polarity is also positioned obliquely across cap (170). First and second electrode surfaces (184, 186) are placed across cap (170) such that the polarity of electrode surfaces (184, 186) is alternating. In FIG. 11, a first electrode surface (188) with a first polarity is positioned in a "U" shaped configuration along cap (170). A second electrode surface (190) with a second, opposite polarity is positioned around first electrode surface (188) in a "U" shaped configuration partially surrounding the "U" shaped configuration of first electrode surface (188). Other suitable electrode configurations will be apparent to one with ordinary skill in the art in view of the teachings herein.

In an exemplary use, electrode cap (170) is coupled to end effector (140). Cap (170) is positioned over jaw (142) and pressed onto jaw (142), as shown in FIG. 5B. Protrusions (178) flex outward when cap (170) is being pressed onto jaw (142). Protrusions (178) then flex inward and insert into engagement recesses (179) to secure cap (170) to jaw (142). End effector (140) is then operated as described above. End effector (140) is inserted into a patient via a trocar. Articulation control (28) may then be manipulated to pivot or flex articulation section (36) of shaft (30) in order to position end effector (140) at a desired position and orientation relative to an anatomical structure within the patient. Two layers of tissue of the anatomical structure are then captured between jaws (142, 144) by squeezing trigger (24) toward pistol grip (22). Flanges (62, 66) cammingly act to pivot jaw (142) toward jaw (144) when firing beam (60) is actuated distally by squeezing trigger (24) toward pistol grip (22). Jaws (142, 144) may be substantially clamping tissue before trigger (24) has swept through a full range of motion toward pistol grip (22), such that trigger (24) may continue pivoting toward pistol grip (22) through a subsequent range of motion after jaws (142, 144) have substantially clamped on the tissue.

With tissue layers captured between jaws (142, 144) firing beam (60) continues to advance distally by the user squeezing trigger (24) further toward pistol grip (22). As firing beam (60) continues to advance distally, distal blade (64) simultaneously severs the clamped tissue layers, resulting in separated upper layer portions being apposed with respective separated lower layer portions. With severed tissue layer portions being compressed between jaws (142, 144), electrode surfaces (150, 152) are activated with bipolar RF energy by the user depressing activation button (26). The bipolar RF energy delivered by power source (80) ultimately electrosurgically welds the tissue layer portions on one side of firing beam (60) together and the tissue layer portions on the other side of firing beam (60) together.

Figure 12:
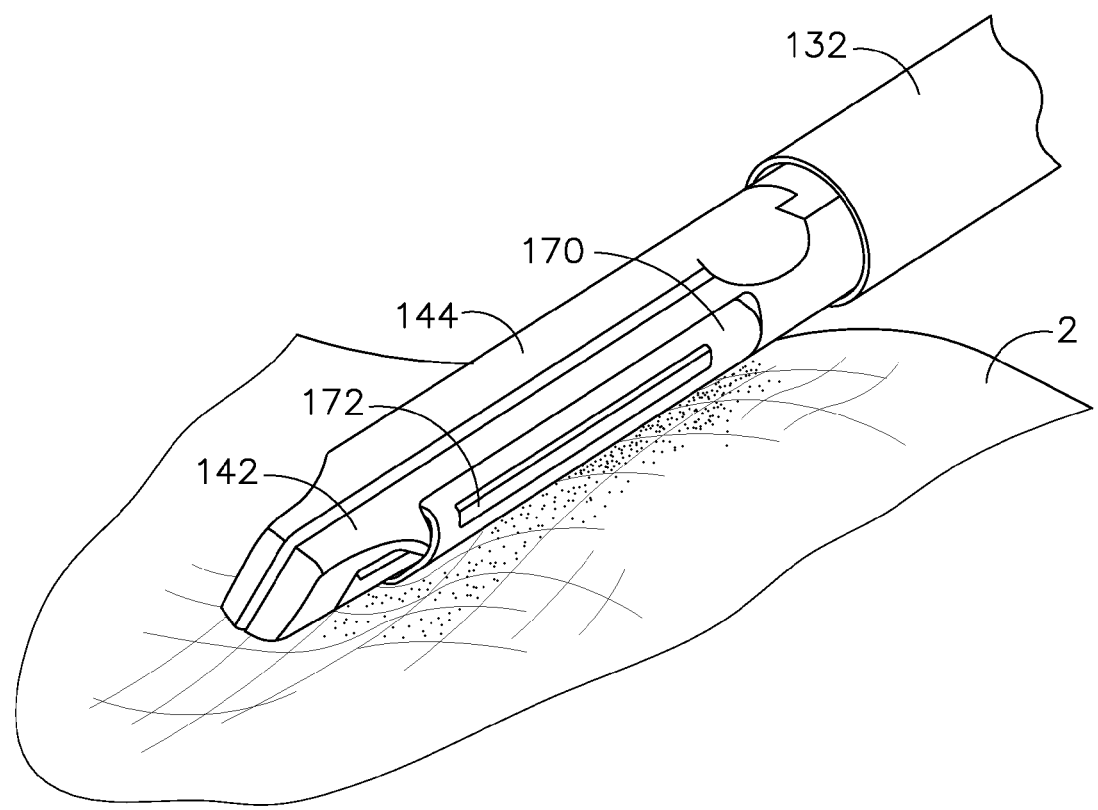
FIG. 12 depicts a perspective view of the end effector of FIG. 5A with the electrode cap pressed against tissue.

Because electrode surfaces (172, 174) of cap (170) are electrically coupled to electrode surfaces (150, 152) of end effector (140), power source (80) also supplies bipolar RF energy to electrode surfaces (172, 174). If a small bleeding source is discovered, the bleeding source may be pinpointed by positioning end effector (140) to apply cap (170) to the desired area of tissue. Cap (170) is pushed into tissue such that electrode surfaces (172, 174) contact the tissue, as shown in FIG. 12. The small bleeding source is positioned between electrode surfaces (172, 174). Electrode surfaces (172, 174) are activated with bipolar RF energy by the user depressing activation button (26). The bipolar RF energy ultimately electrosurgically welds the small bleeding source.

Figure 13A:
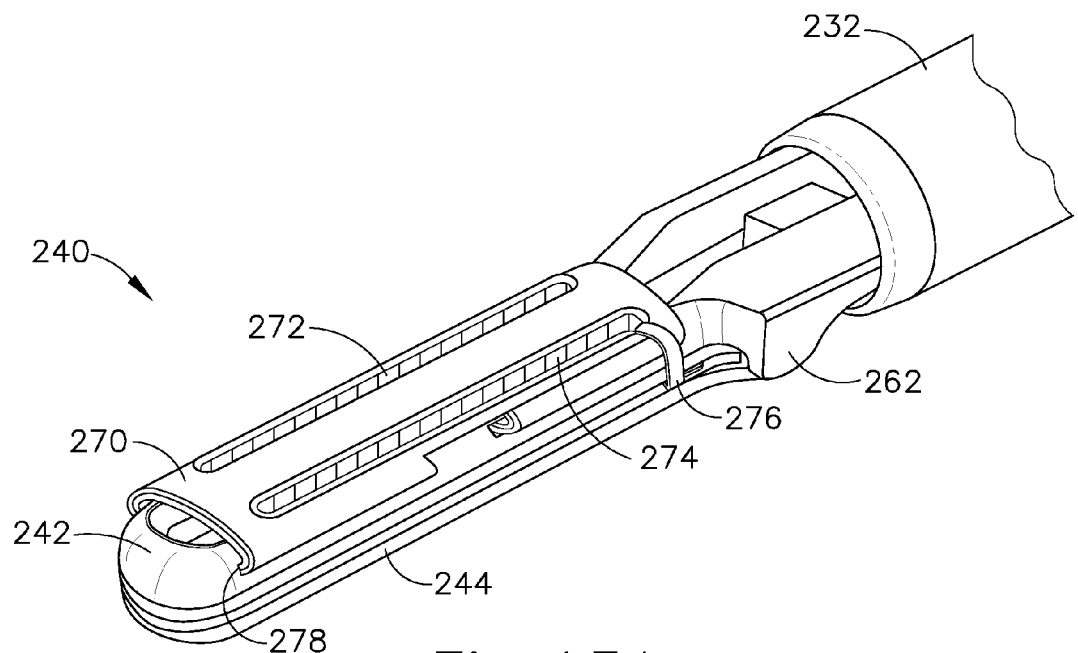
FIG. 13A depicts a top perspective view of another exemplary end effector for use with the instrument of FIG. 1, in a closed position showing an electrode cap with a color-changing material.
Figure 13B:
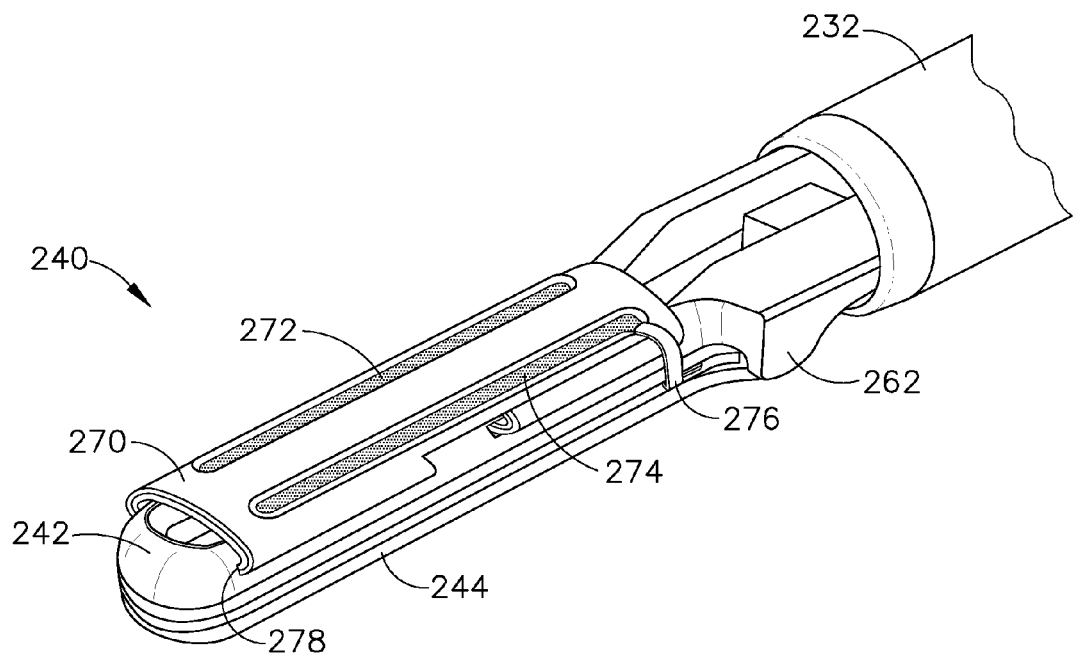
FIG. 13B depicts a top perspective view of the end effector of FIG. 13A, in a closed position showing the electrode cap with the color-changing material in a ready-to-use state.

In some versions, an electrode cap (270) is provided with a visual feedback to indicate the electrode surfaces (272, 274) are energized. Visual feedback that electrode surfaces (272, 274) are energized may prevent inadvertent contact with tissues other than those where coagulation is wanted. Visual feedback also shows the boundaries of electrode surfaces (272, 274) to help place electrode surfaces (272, 274) in the desired area. FIGS. 13A-13B show electrode cap (270) for coupling with an end effector (240) with visual feedback. End effector (240) is similar to end effector (140). Cap (270) is similar to cap (170), except that cap (270) comprises electrode surfaces (272, 274) that provide visual feedback. A color changing material or paint is mixed in with the material of electrode surfaces (272, 724). Alternatively, the color changing material or paint may be applied to the exterior of electrode surfaces (272, 274). A thin laminate coating, about 1 to about 2 mm thick, of the color changing material can then be adhered over electrode surfaces (272, 274). This coating can be doped to be electrically conductive in the areas over electrode surfaces (272, 274). The coating may be biocompatible. Various suitable materials and techniques for incorporating such materials will be apparent to one with ordinary skill in the art in view of the teachings herein.

The color changing material is configured to react to heat in the present example, though the material may also/alternatively be configured to react to other conditions (e.g. RF current, etc.). When electrode surfaces (272, 274) are de-energized, color changing material may be in a neutral state (FIG. 13A). When electrode surfaces (272, 274) are energized, the energy provided to electrode surfaces (272, 274) heats the electrode surfaces (272, 274) and the color changing material. The color changing material is then in a heated state and changes to a color (FIG. 13B). For example, the color changing material may change to a bright red, orange, or yellow color to provide visual feedback to the user that electrode surfaces (272, 274) are energized. Alternatively, the color changing material may change from a first color to a second color when the color changing material transitions between the neutral state to the heated state. The color changing material may also be configured to phosphoresce in response to actuation of electrode surfaces (272, 274). The color changing material may also change color or states in stages as the temperature of electrode surfaces (272, 274) increases. Other suitable color configurations will be apparent to one with ordinary skill in the art in view of the teachings herein. In some versions, the color changing material may react based on the transfer of energy instead of heat.

In an exemplary use, electrode cap (270) is coupled to end effector (240), as shown in FIG. 13A. Cap (270) is positioned over jaw (242) and pressed onto jaw (242). Protrusions (278) flex outward when cap (270) is being pressed onto jaw (242). Protrusions (278) then flex inward and insert into engagement recesses (279) to secure cap (270) to jaw (242). In the de-energized state, electrode surfaces (272, 274) are not heated, and the color changing material is in a neutral state, as shown in FIG. 13A. End effector (240) is then operated as described above to electrosurgically seal tissue layer portions. Because electrode surfaces (272, 274) of cap (270) are electrically coupled to electrode surfaces (250, 252) of end effector (240), power source (80) also supplies bipolar RF energy to electrode surfaces (272, 274). When power source (80) supplies bipolar RF energy to electrode surfaces (272, 274), electrode surfaces (272, 274) are heated, thereby heating the color changing material. The color changing material then changes to the heated state, displaying a bright color, as shown in FIG. 13B. With color changing material in the heated state, electrode surfaces (272, 274) are visually colored to provide visual feedback to the user that electrode surfaces (272, 274) are energized and to indicate the physical boundaries of electrode surfaces (272, 274). If a small bleeding source is discovered, the bleeding source may be pinpointed by positioning end effector (240) to apply cap (270) to the desired area of tissue. Cap (270) is pushed into tissue such that electrode surfaces (272, 274) contact the tissue. The small bleeding source is positioned between electrode surfaces (272, 274). The bipolar RF energy ultimately electrosurgically welds the small bleeding source. After the RF energy is removed from electrode surfaces (272, 274), electrode surfaces (272, 274) may cool. The color changing material may then return to the neutral state. The visual feedback of electrode surfaces (272, 274) may enable a surgeon to see the state of electrode surfaces (272, 274) without having to look away from a monitor that is displaying an endoscopic image of the surgical field.

B. Exemplary Electrode Cap with a Powered Tip

Figure 14:
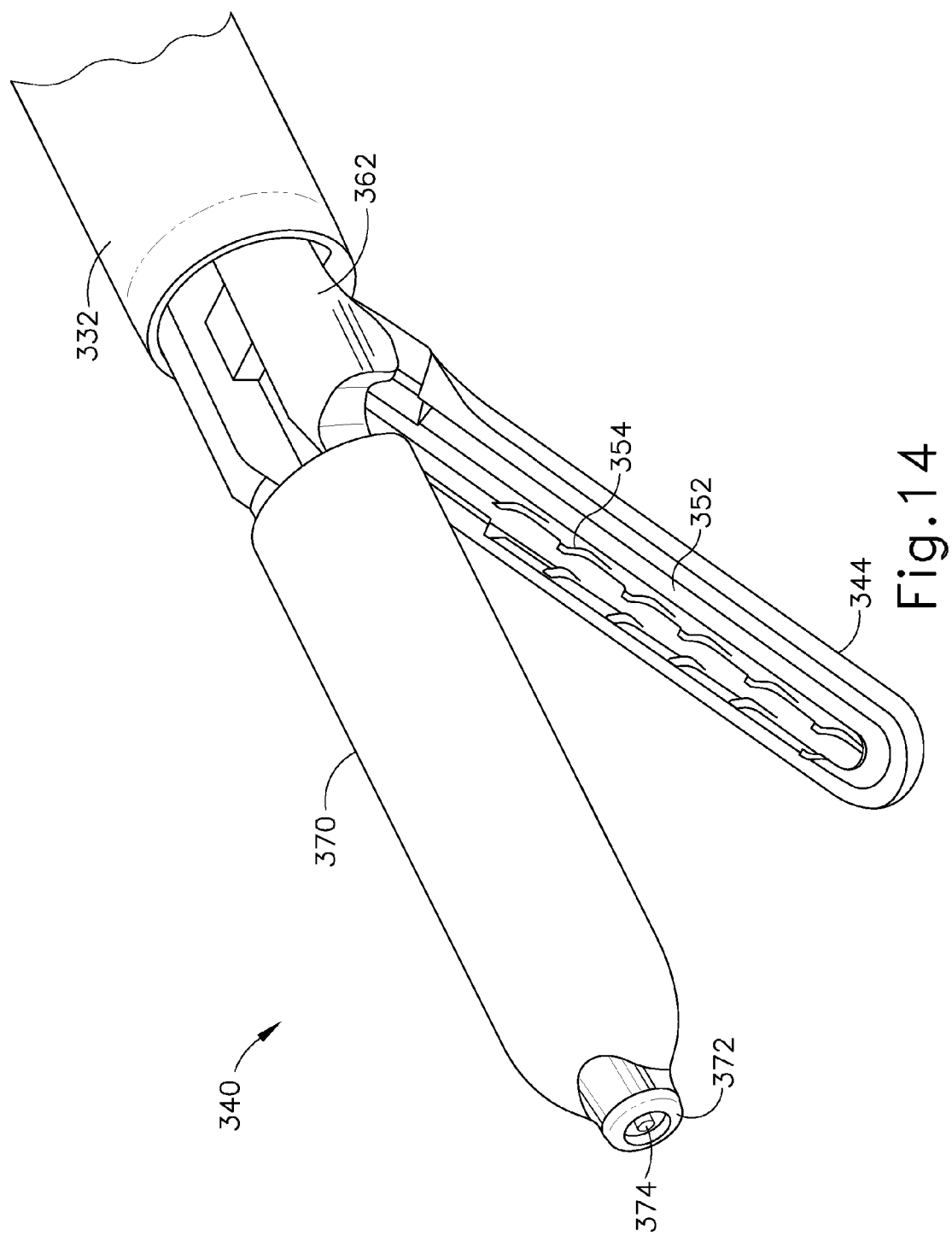
FIG. 14 depicts a top perspective view of another exemplary end effector for use with the instrument of FIG. 1, in an open position showing an electrode cap having an end electrode.
Figure 17A:
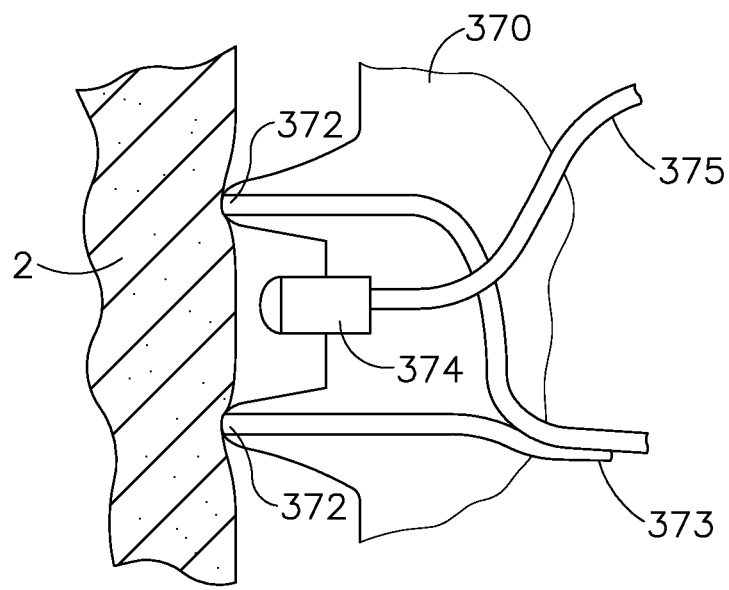
FIG. 17A depicts a cross-sectional view of the electrode cap of FIG. 14 pressed against tissue in a deactivated state.
Figure 17B:
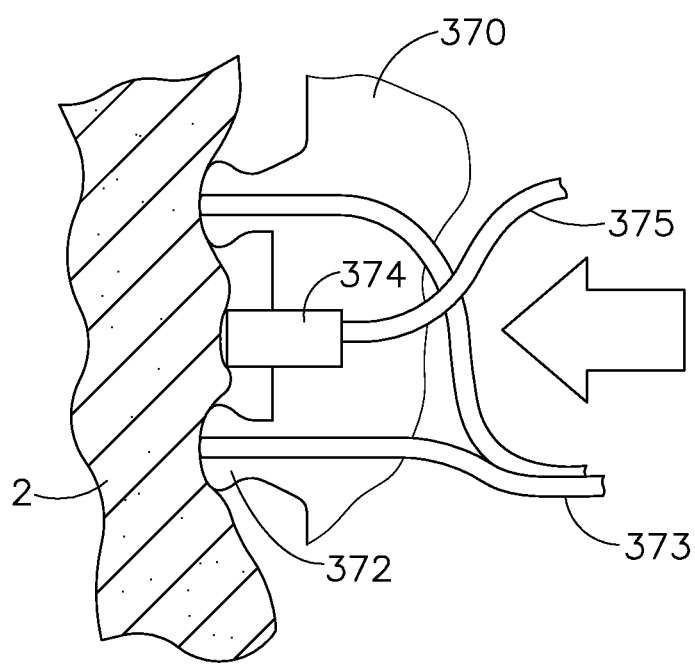
FIG. 17B depicts a cross-sectional view of the electrode cap of FIG. 14 pressed against tissue in an activated state.

FIGS. 14-17B show an exemplary electrode cap (370) for coupling with an end effector (340). End effector (340) is similar to end effector (140). Electrode cap (370) is similar to electrode cap (170), except that electrode cap (370) includes electrode surfaces (372, 374) at the tip of cap (370), as shown in FIG. 14. With both electrode surfaces (372, 374) positioned on the end of the same jaw (342), the bipolar efficiency may be improved by limiting energy through the system. Electrode cap (370) is sized to couple to the exterior surface of stationary jaw (342). This may prevent wiring to cap (370) from needing to bend with pivoting jaw (344). Cap (370) comprises electrode surfaces (372, 374), wires (373, 375), and an electrode coupling feature (376), as shown in FIG. 15. Electrode surfaces (372, 374) are positioned on the tip of cap (370). First electrode surface (372) is in an annular configuration. Second electrode surface (374) is coaxially positioned within first electrode surface (372). Second electrode surface (374) is slightly recessed into cap (370) relative to first electrode surface (372), as shown in FIG. 17A. Because second electrode surface (374) is slightly recessed relative to first electrode surface (372), first electrode surface (372) is slightly deformable. Deformability may be accomplished by suspending first electrode surface (372) within an elastomeric button. With electrode surfaces (372, 374) recessed relative to one another, cap (370) is applied to tissue until first electrode surface (372) deforms to allow the tissue to contact second electrode surface (374), as shown in FIG. 17B. This compression provides sufficient contact with the tissue to improve the weld. In other words, it requires at least a certain amount of pressure to be applied against the tissue before RF energy may be applied.

First electrode surface (372) is configured at a first polarity and second electrode surface (374) is configured at a second (opposite) polarity, such that RF current flows through conductive material (e.g. tissue) that is positioned between electrode surfaces (372, 374). As best seen in FIG. 15, wire (373) extends from first electrode surface (372) to jaw (342) to provide a first polarity of RF energy via jaw (342). Wire (375) extends from second electrode surface (374) to electrode coupling feature (376) to provide a second polarity of RF energy that is opposite to the polarity provided through first electrode surface (372).

In an exemplary use, electrode cap (370) is coupled to end effector (340), as shown in FIG. 14. Cap (370) is positioned over jaw (342) and pressed onto jaw (342). Cap (370) may comprise protrusions similar to protrusions (278) and jaw (342) may comprise engagement recesses similar to engagement recesses (279). The protrusions flex outward when cap (370) is being pressed onto jaw (342). The protrusions may then flex inward and insert into the engagement recesses to secure cap (370) to jaw (342). End effector (340) may then be operated as described above to electrosurgically seal tissue layer portions. If a small bleeding source is detected, end effector (340) may be positioned over the small bleeding source such that the tip of cap (370) is positioned over the small bleeding source, as shown in FIG. 17A. Power source (80) is configured to supply bipolar RF energy to electrode surfaces (372, 374) via wires (373, 375). The tip of cap (370) is pushed into tissue. As cap (370) is pushed against the tissue, first electrode surface (372) deforms proximally to allow tissue to also contact second electrode surface (374), as shown in FIG. 17B. This allows the bipolar RF energy to pass from electrode surface (374), through tissue, to electrode surface (372) to ultimately electrosurgically weld the small bleeding source. In some versions, electrode surfaces (372, 374) receive RF energy whenever electrodes of jaws (342, 344) receive RF energy. In some other versions, electrode surfaces (372, 374) receive RF energy independently relative to electrodes of jaws (342, 344). This may vary based on the configurations of wires (373, 375), etc.

Figure 18A:
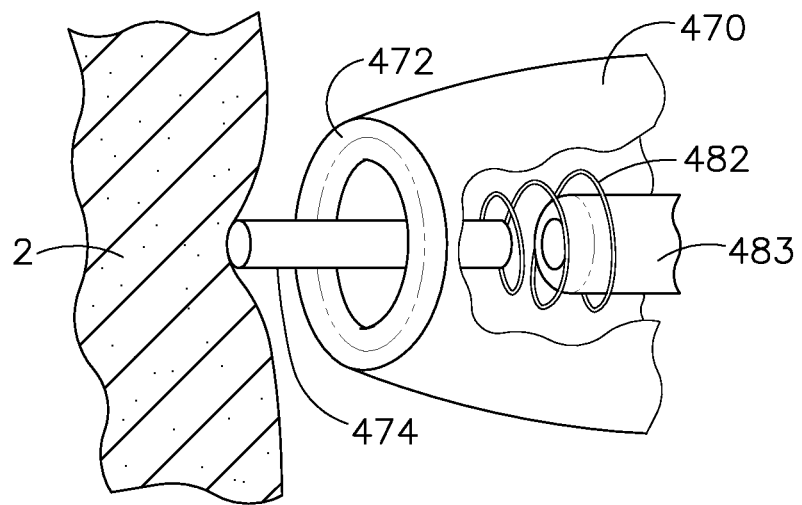
FIG. 18A depicts a cross-sectional view of another variation of the electrode cap of FIG. 14, with a resilient electrode pressed against tissue in a deactivated state.
Figure 18B:
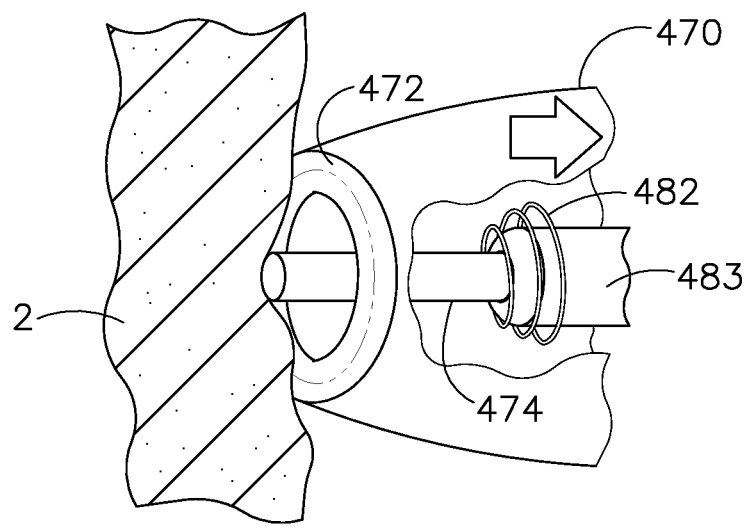
FIG. 18B depicts a cross-sectional view of the electrode cap of FIG. 18A, with a resilient electrode pressed against tissue in an activated state.

In some versions, an electrode is resiliently biased such that the electrode is configured as a switch. For instance, FIGS. 18A-18B show another exemplary electrode cap (470) with a resiliently biased second electrode (474). Electrode cap (470) is similar to electrode cap (370), except that the second electrode (474) comprises a resilient member (482). In a de-energized state, second electrode (474) protrudes from cap (470) and extends past first electrode (472), as shown in FIG. 18A. Resilient member (482) is positioned proximal to second electrode (474) to bias second electrode (474) distally. In the distal position, second electrode (474) is de-coupled from wire (483) such that second electrode (474) is de-activated. When the tip of cap (470) is pushed into tissue to electrosurgically weld a portion of tissue, the tissue pushes second electrode (474) to a proximal position, as shown in FIG. 18B. In the proximal position, second electrode (474) compresses resilient member (482) to contact wire (483). This energizes second electrode (474) to an activated state. Second electrode (474) also aligns with first electrode (472) in the proximal position. This allows the bipolar RF energy to pass through tissue between electrodes (472, 474) to ultimately electrosurgically weld the small bleeding source.

Figure 19A:
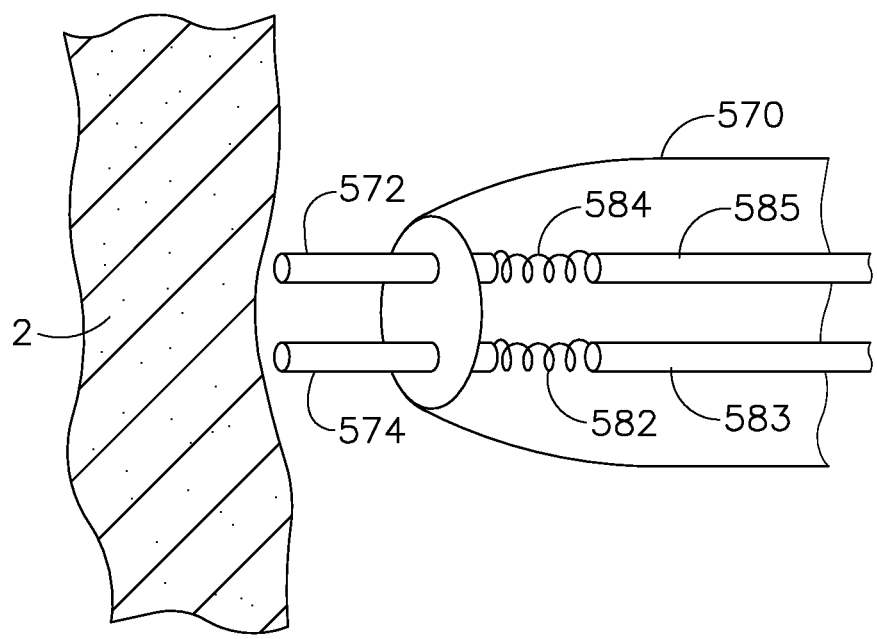
FIG. 19A depicts a cross-sectional view of another variation of the electrode cap of FIG. 14, with a pair of resilient electrodes pressed against tissue in a deactivated state.
Figure 19B:
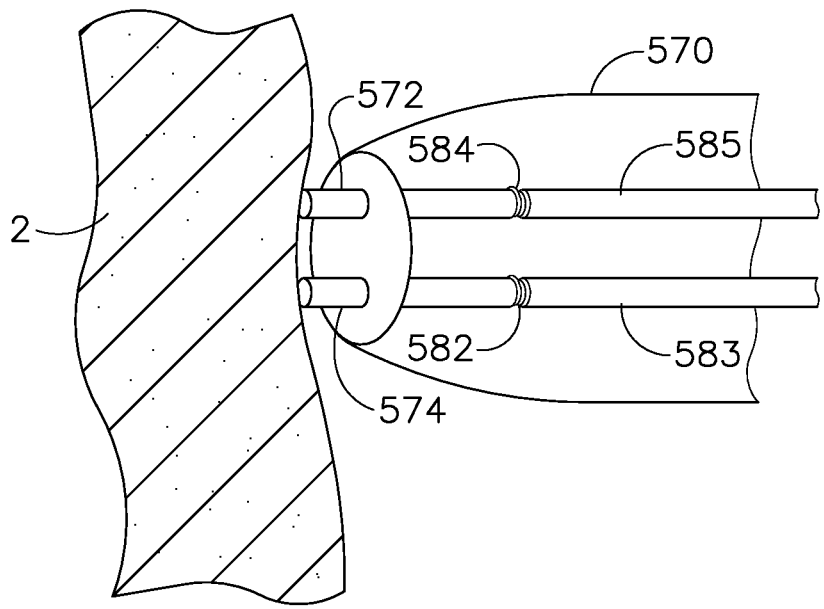
FIG. 19B depicts a cross-sectional view of the electrode cap of FIG. 19A, with a pair of resilient electrodes pressed against tissue in an activated state.

In some versions, a pair of electrodes are resiliently biased such that the electrodes are configured as a switch. FIGS. 19A-19B show another exemplary electrode cap (570) with resiliently biased first and second electrodes (572, 574). Electrode cap (570) is similar to electrode cap (470), except that each electrode (572, 574) comprises a resilient member (582, 584). Electrodes (572, 574) protrude from cap (570). Resilient members (582, 584) are positioned proximal to electrodes (572, 574) to bias electrodes (572, 574) distally. In the distal position electrodes (572, 574) are de-coupled from wires (583, 585) such that electrodes (572, 574) are de-activated, as shown in FIG. 19A. When the tip of cap (570) is pushed into tissue to electrosurgically weld a portion of tissue, the tissue pushes electrodes (572, 574) to a proximal position, as shown in FIG. 19B. In the proximal position, electrodes (572, 574) compress resilient members (582, 584) to contact wires (583, 585). This energizes electrodes (572, 574) to an activated state. This allows the bipolar RF energy to pass through tissue between electrodes (572, 574) to ultimately electrosurgically weld the small bleeding source.

Figure 20A:
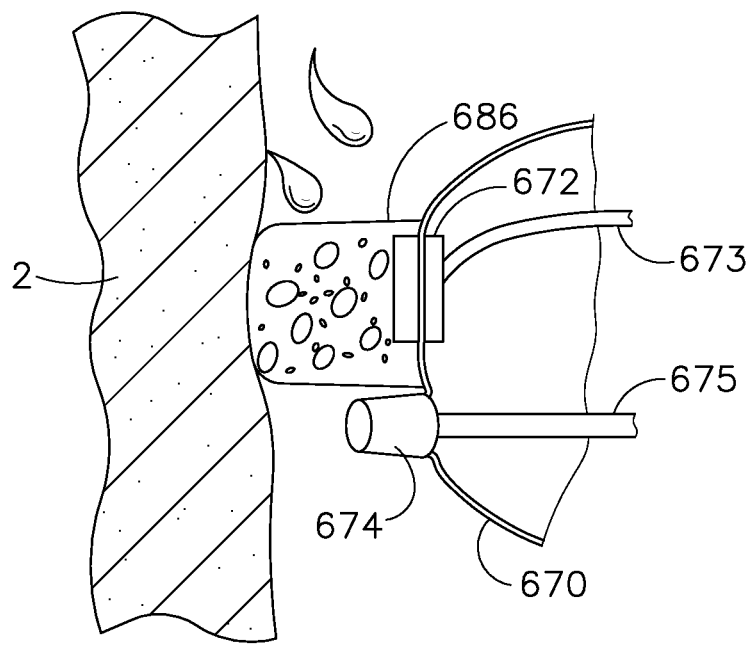
FIG. 20A depicts a cross-sectional view of another variation of the electrode cap of FIG. 14, with a sponge electrode pressed against tissue in a deactivated state.
Figure 20B:
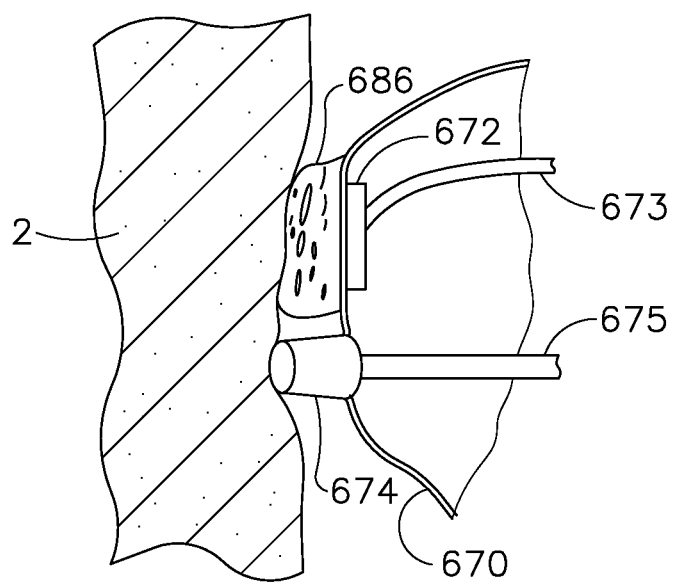
FIG. 20B depicts a cross-sectional view of the electrode cap of FIG. 20A, with a sponge electrode pressed against tissue in an activated state.

In some versions, an electrode is positioned within a salt saturated sponge or similar feature such that the electrode is configured as a switch. For instance, FIGS. 20A-20B show another exemplary electrode cap (670) with a salt saturated sponge (686). Electrode cap (670) is similar to electrode cap (370), except that first electrode (672) is positioned within a salt saturated sponge (686). Electrodes (672, 674) are positioned in the tip of cap (670) and are in continuous contact with wires (673, 675). In a de-energized state, sponge (686) extends past second electrode (674), as shown in FIG. 20A. Sponge (686) is substantially dry and non-conductive in this state. When the tip of cap (670) is pushed into tissue to electrosurgically weld a portion of tissue, the tissue saturates sponge (686) with bodily fluid (e.g. blood). As sponge (686) is saturated, sponge (686) compresses to align with second electrode (672), as shown in FIG. 20B. Sponge (686) becomes conductive when saturated to conduct the energy from first electrode (672). This allows the bipolar RF energy to pass through tissue between sponge (686) and second electrode (674) to ultimately electrosurgically weld the small bleeding source.

C. Exemplary Electrode Blade

Figure 21:
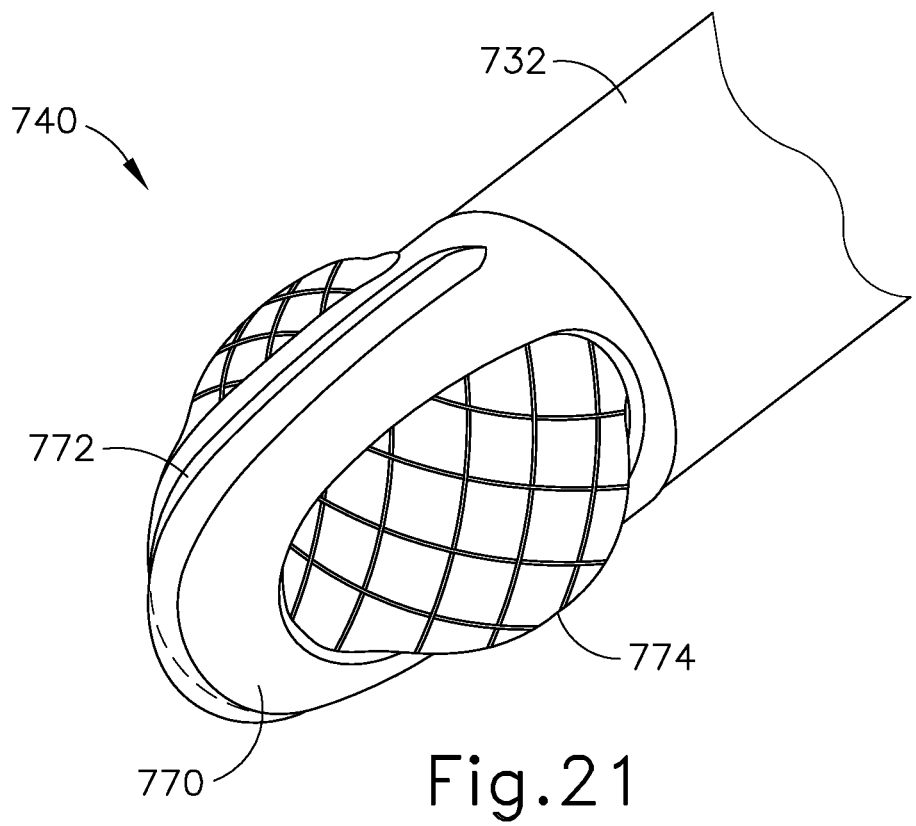
FIG. 21 depicts a top perspective view of another exemplary end effector for use with the instrument of FIG. 1.
Figure 22:
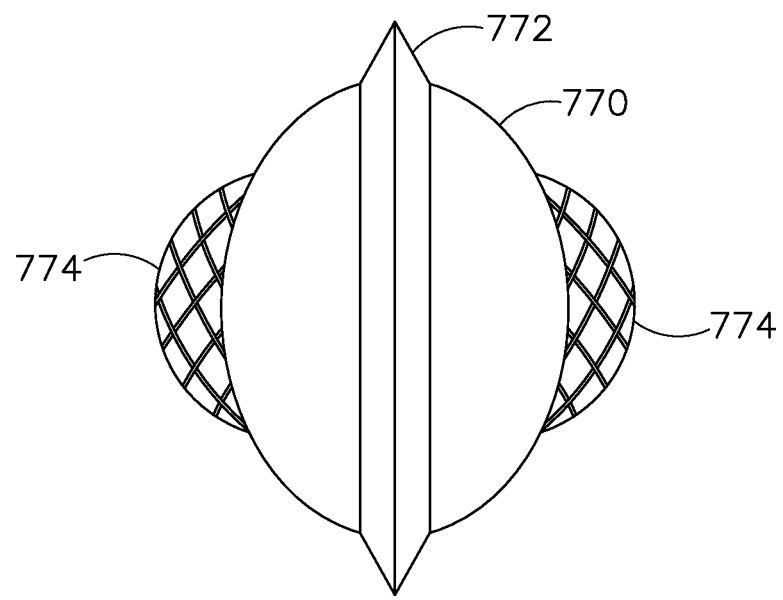
FIG. 22 depicts an end view of the end effector of FIG. 21.
Figure 23:
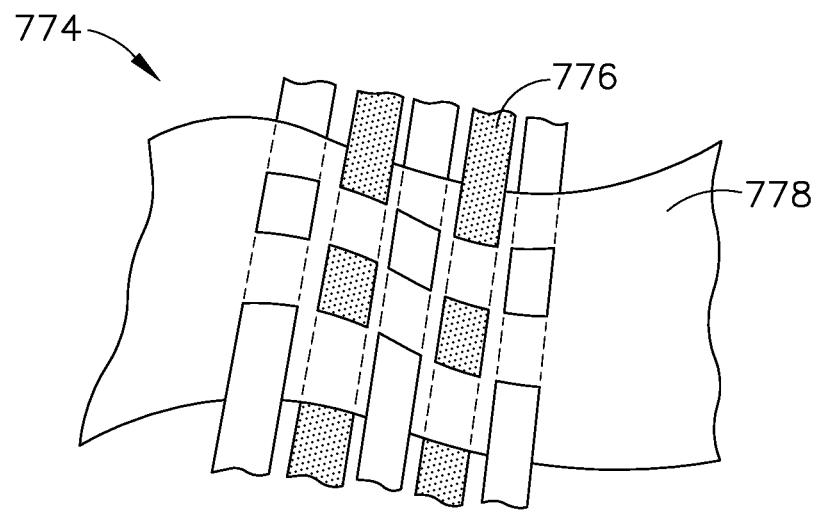
FIG. 23 depicts a perspective view of an electrode configuration of the end effector of FIG. 21.

FIGS. 21-24 show an exemplary end effector (740) with an electrode blade (772) for coupling with an end effector sheath (732). End effector (740) may also be provided as a standalone instrument. End effector (740) may act as a deformable blunt dissector, a tissue separator, or a bipolar coagulation tip when energized. Sheath (732) is similar to sheath (32) described above. In some instances, shaft (30) is configured to selectively accept end effector (40) or end effector (740), providing a degree of modularity. End effector (740) of this example comprises a tip (770), an electrode blade (772), electrode lobes (774), as shown in FIGS. 21-22. Blade (772) is positioned along the center of tip (770) and wraps around at least a portion of tip (770). Lobes (774) are positioned on opposing sides of tip (770). Blade (772) is configured at a first polarity. Blade (772) may be made of a highly deformable metallic such as nitinol or 6065 aluminum. Other suitable materials will be apparent to one with ordinary skill in the art in view of the teachings herein. Tip (770) is deformable to allow for improved tissue contact. The center of sheath (732) and tip (770) are filled with a highly heat conductive aluminum rod surrounded by a saline, which is kept under pressure. The aluminum rod is also electrically coupled to flexible lobes (774). Lobes (774) are configured at a second (opposite) polarity to blade (772), such that RF current flows through tissue positioned between blade (772) and either or both of lobes (774). Lobes (774) comprise a base (778) with members (776) woven through base (778), as shown in FIG. 23. Base (778) may be made of either highly deformable conductive gel or woven Kevlar fabric. Members (776) may be made of either electrically conductive woven nitinol wires, carbon fibers with high carbon-carbon contact, and/or aluminum wires. The gaps in the weave of lobes (774) allow saline to seep through. Lobes (774) serve as electrode membranes, by allowing for a limited amount of saline leakage to improve electrode tissue coupling/conductivity and electrode cooling. Various other suitable materials that may be used to form members (776) and/or base (778) will be apparent to one with ordinary skill in the art in view of the teachings herein. Lobes (774) are asymmetric and highly deformable to diffuse pressure contact with tissue.

Figure 24:
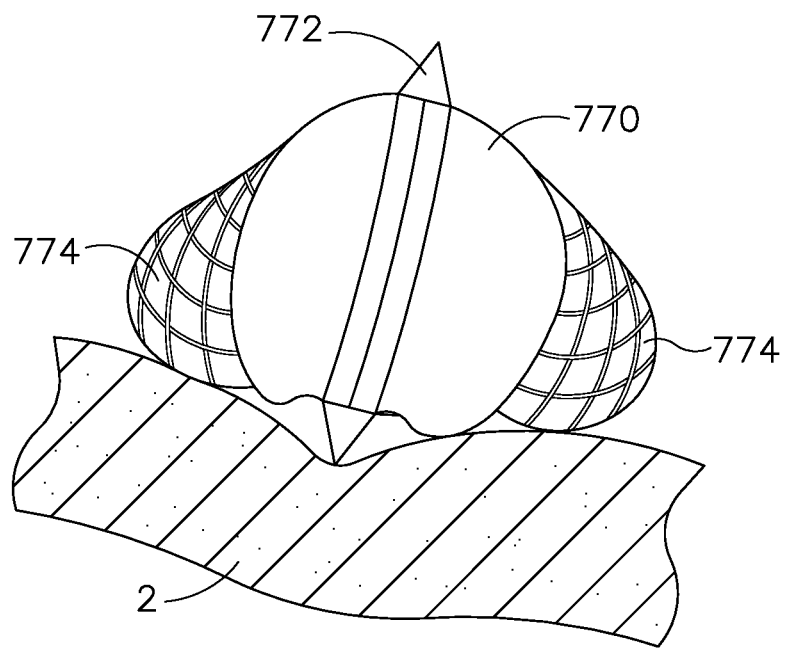
FIG. 24 depicts a perspective view of the end effector of FIG. 21 cutting tissue.

In an exemplary use, end effector (740) is coupled to sheath (732). End effector (740) is inserted into a patient via a trocar. Blade (772) may be used to sever tissue (2). Alternatively, if a small bleeding source is detected, tip (770) may be placed on the small bleeding source and end effector (740) may deliver RF energy to electrosurgically seal the tissue. The small bleeding source is positioned between electrode surfaces of blade (772) and either or both of lobes (774). Blade (772), lobes (774), and tip (770) all deform to provide sufficient contact of end effector (740) with the tissue, as shown in FIG. 24. Blade (772) and lobes (774) are activated with bipolar RF energy by the user depressing activation button (26). The bipolar RF energy delivered by power source (80) ultimately electrosurgically welds the tissue layer portions. The RF energy may also be delivered while blade (772) severs tissue (2) to simultaneously weld tissue (2). It should therefore be understood that end effector (740) may be used for tissue dissection and/or just for "bleeder touch up" purposes, as desired. Even when not energized, end effector (740) may still be used to perform blunt dissection and other tasks.

Figure 25:
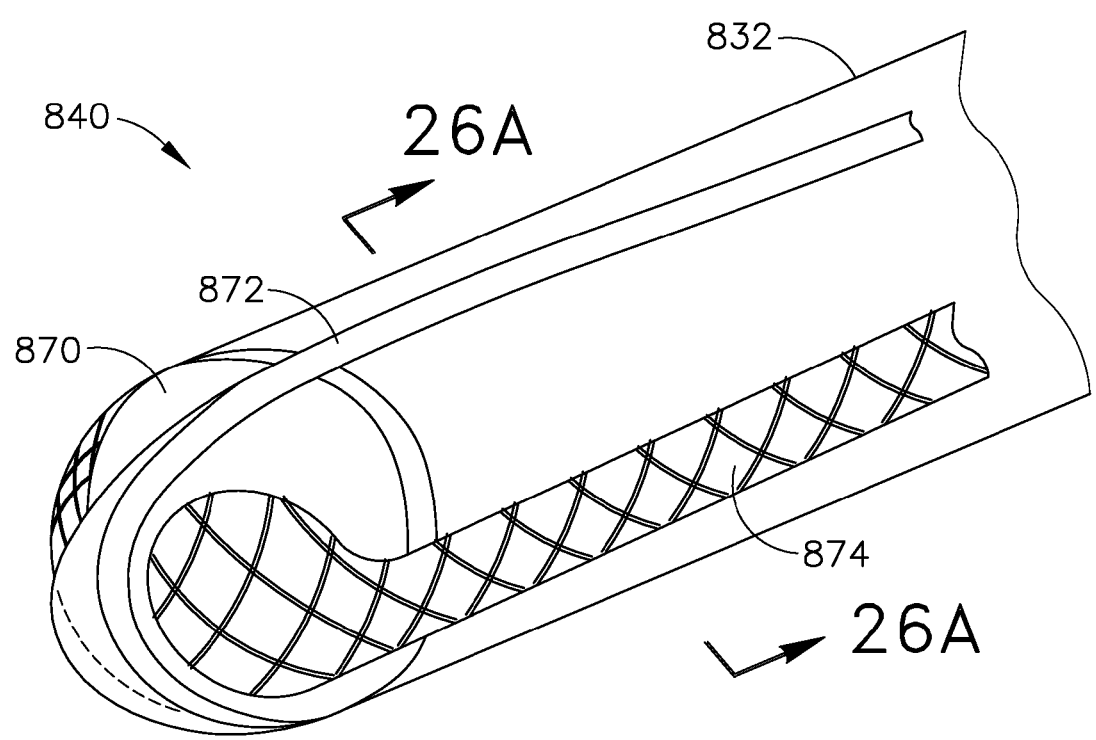
FIG. 25 depicts a perspective view of a variation of the end effector of FIG. 21 showing another exemplary electrode configuration.
Figure 26A:
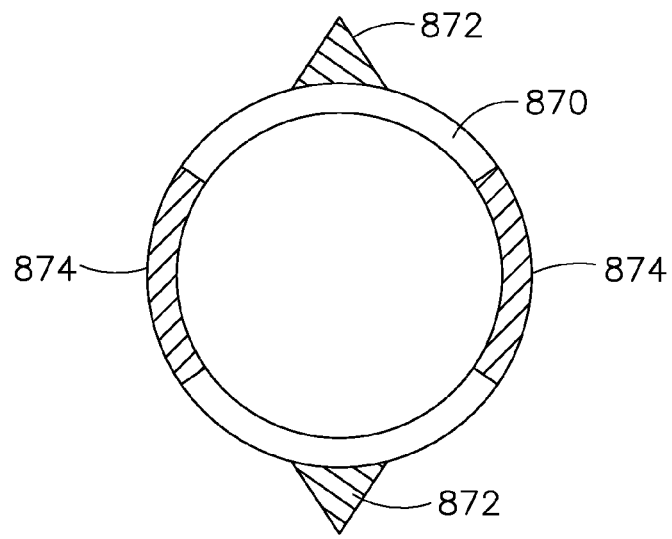
FIG. 26A depicts an end view of the end effector of FIG. 25.
Figure 26B:
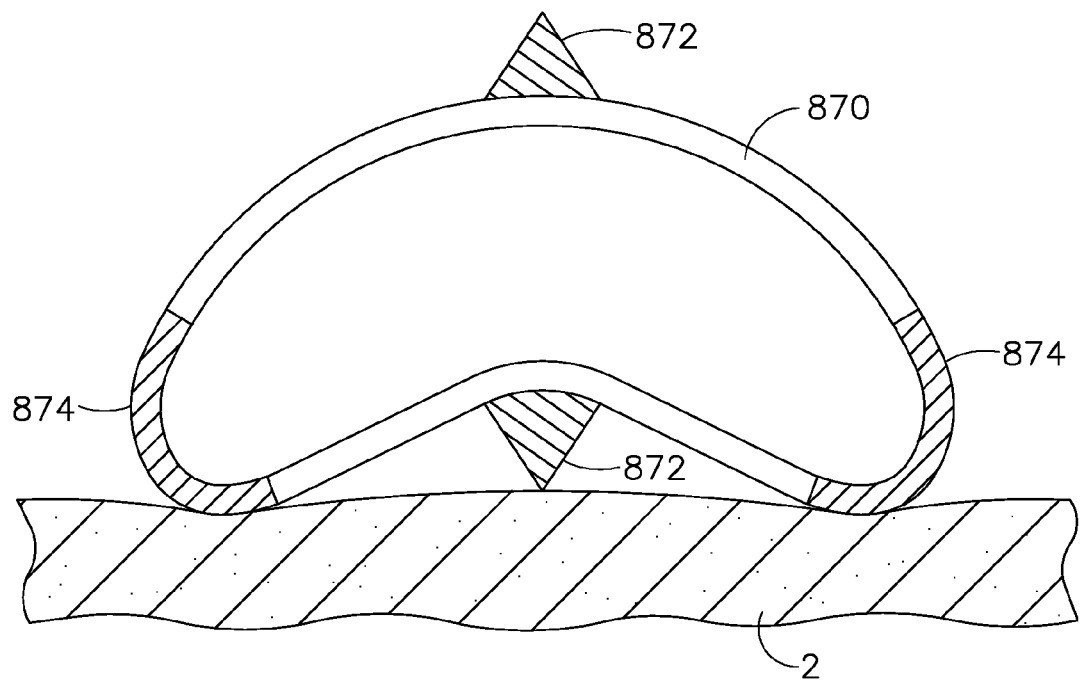
FIG. 26B depicts an end view of the end effector of FIG. 25 cutting tissue.

FIGS. 25-26B show an exemplary end effector (840) where blade (872) and electrode lobes (874) extend past tip (870) and along sheath (832). End effector (840) may be coupled to sheath (832), or provided as a standalone instrument. End effector (840) is similar to end effector (740), except that blade (872) and lobes (874) of end effector (840) are extended, as shown in FIG. 25. This may allow for an increased area where RF energy is provided. If a bleeding source is detected, tip (870) may be placed over the bleeding source and end effector (840) may deliver RF energy to electrosurgically seal the tissue. The bleeding source is positioned between the electrode surfaces of blade (872) and lobes (874). Blade (872), lobes (874), and/or tip (870) deform to provide sufficient contact of end effector (840) with the tissue, as shown in FIG. 26B. Blade (872) and lobes (874) are activated with bipolar RF energy by the user depressing activation button (26). The bipolar RF energy delivered by power source (80) ultimately electrosurgically welds the tissue layer portions. The RF energy may also be delivered while blade (872) severs tissue (2) to simultaneously weld tissue (2).

FIGS. 27A-27C show an exemplary end effector (940) where blade (972) is positioned on one side of tip (970). End effector (940) is similar to end effector (840), except that blade (972) extends on only one side of tip (970), as shown in FIG. 27A. Electrode lobes (974) are also positioned closer to blade (972) to extend along the same side of tip (970). If a bleeding source is detected, tip (970) may be placed over the bleeding source and end effector (940) may deliver RF energy to electrosurgically seal the tissue. The bleeding source is positioned between the electrode surfaces of blade (972) and lobes (974). Blade (972), lobes (974), and/or tip (970) deform to provide sufficient contact of end effector (940) with the tissue, as shown in FIG. 27B. Blade (972) and lobes (974) are activated with bipolar RF energy by the user depressing activation button (26). The bipolar RF energy delivered by power source (80) ultimately welds the tissue layer portions. The RF energy may also be delivered while blade (972) severs tissue (2) to simultaneously weld tissue (2), as shown in FIG. 27C.

FIGS. 28A-28B show an exemplary end effector (1040) where blade (1072) and electrode beams (1074) are configured to spread apart when end effector (1040) is depressed onto tissue (2). This may provide an increased welded area between blade (1072) and beams (1074). End effector (1040) may be coupled to a shaft (30), or provided as a standalone instrument. End effector (1040) is similar to end effector (940), except that blade (1072) and beams (1074) are positioned within a retractable sheath (1070), as shown in FIG. 28A. Sheath (1070) comprises an open distal end such that blade (1072) and beams (1074) extend out of sheath (1070). Blade (1072) and beams (1074) are aligned across sheath (1070). When sheath (1070) is in a distal position, beams (1074) are positioned near blade (1072), as shown in FIG. 28A. When sheath (1070) is translated to a proximal position, beams (1074) splay outwardly from blade (1072), as shown in FIG. 28B. A camming member (not shown) having angled surfaces may be provided in sheath (1070) between beams (1074 and blade (1072). As sheath (1070) is translated proximally, the camming member may translate with sheath (1070) such that the angled surfaces push apart beams (1074). As another merely illustrative alternative, beams (1074) may be resiliently biased to splay outwardly, such that sheath (1070) forces beams (1074) to assume a substantially straight configuration when sheath (1070) is advanced to a distal position. Other suitable features to spread apart beams (1074) will be apparent to one with ordinary skill in the art in view of the teachings herein.

If a bleeding source is detected, sheath (1070) may be placed over the bleeding source and end effector (1040) may deliver RF energy to electrosurgically seal the tissue. Sheath (1070) is translated proximally to deform beams (1074) outwardly from blade (1072) to increase the sealing area, as shown in FIG. 28B. The splaying of beams (1074) may also place the tissue in tension by stretching the tissue, facilitating cutting by blade (1072). The bleeding source is positioned between the electrode surfaces of blade (1072) and beams (1074). Blade (1072) and beams (1074) are activated with bipolar RF energy by the user depressing activation button (26). The bipolar RF energy delivered by power source (80) ultimately welds the tissue layer portions. The RF energy may also be delivered while blade (1072) severs tissue (2) to simultaneously weld tissue (2). In some versions, beams (1074) splay to assist in tissue dissection with blade (1072); while beams (1074) may be held substantially straight when end effector (1040) is only used for "bleeder touch up" purposes (e.g., when tissue is not being dissected by blade (1072)).

D. Exemplary Electrode Tip

FIGS. 29-31B show an exemplary end effector (1140) with an electrode tip (1170) for coupling with an end effector sheath (1132). End effector (1140) may act as a bipolar coagulation tip when energized. Alternatively, end effector (1140) may be provided as a standalone instrument. Sheath (1132) is similar to sheath (32) described above. End effector (1140) comprises a tip (1170) and a center rod (1171) positioned within tip (1170). Tip (1170) is configured to be deformable, while center rod (1171) is substantially rigid. Tip (1170) comprises an engagement protrusion (1176), a plurality of first electrode surfaces (1172), and a plurality of second electrode surfaces (1174) such that first electrode surfaces (1172) and second electrode surfaces (1174) are alternating within tip (1170), as shown in FIGS. 30A-30B. Insulators (1173) are positioned between first electrode surfaces (1172) and second electrode surfaces (1174). Insulators (1173) are formed of a non-conductive material so that electrode surfaces (1172) and (1174) are not in electrical communication with each other. First electrode surface (1172) is configured to operate at a first polarity and second electrode surface (1174) is configured at a second (opposite) polarity, such that RF current flows through tissue positioned between electrode surfaces (1172, 1174). Each first electrode surface (1172) comprises a conductive protrusion (1175) extending inwardly into tip (1170).

Figure 31A:
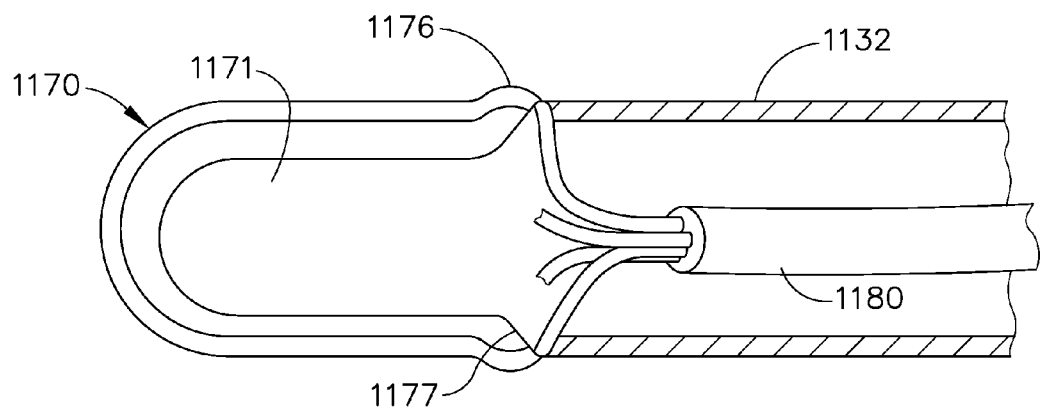
FIG. 31A depicts a cross-sectional side view of the end effector of FIG. 29.

Center rod (1171) is substantially rigid. Center rod (1171) comprises an engagement protrusion (1177) that corresponds to the engagement protrusion (1176) of tip (1170), as shown in FIG. 31A. Engagement protrusion (1177) extends into engagement protrusion (1176) to prevent tip (1170) from translating relative to rod (1171). Rod (1171) is configured to operate at the first polarity with first electrode surface (1172). Wires connect rod (1171) to power source (80) through wire sheath (1180). Separate wires connect second electrode surface (1174) to power source (80) through wire sheath (1180). The separate wires for rod (1171) and second electrode surface (1174) are insulated relative to each other through wire sheath (1180). Alternatively, the separate wires for rod (1171) and second electrode surface (1174) may run independently to power source (80) without a wire sheath (1180). First electrode surface (1172) is not persistently coupled to power source (80). Rod (1171) is configured to contact protrusion (1175) of first electrode surface (1172) when tip (1170) deforms to energize first electrode surface (1172), thereby coupling first electrode surface (1172) with power source (80).

Figure 29:
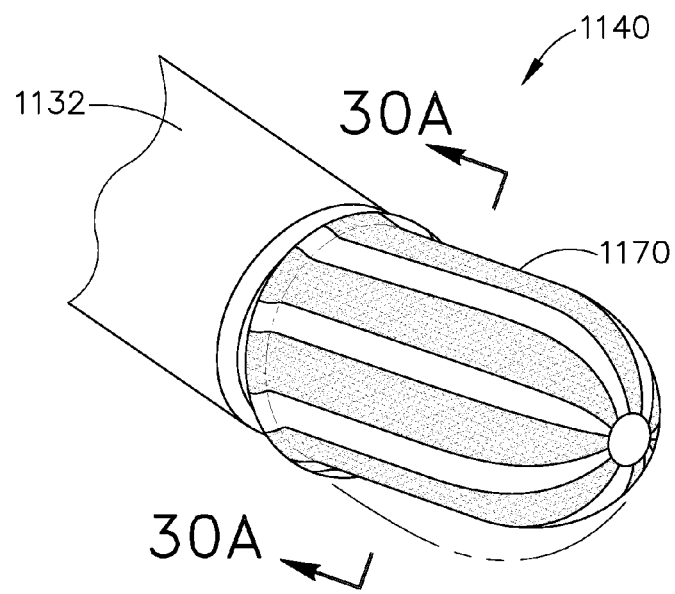
FIG. 29 depicts a perspective view of another exemplary end effector for use with the instrument of FIG. 1.
Figure 30A:
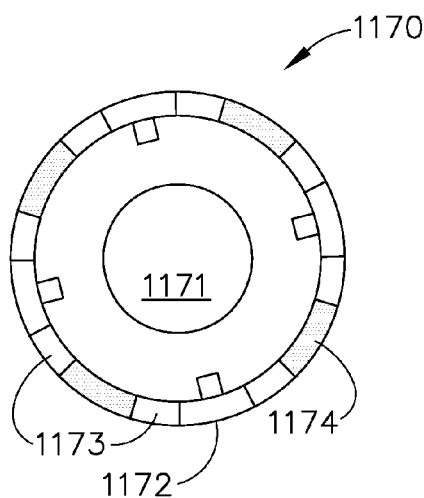
FIG. 30A depicts a cross-sectional end view of the end effector of FIG. 29.
Figure 30B:
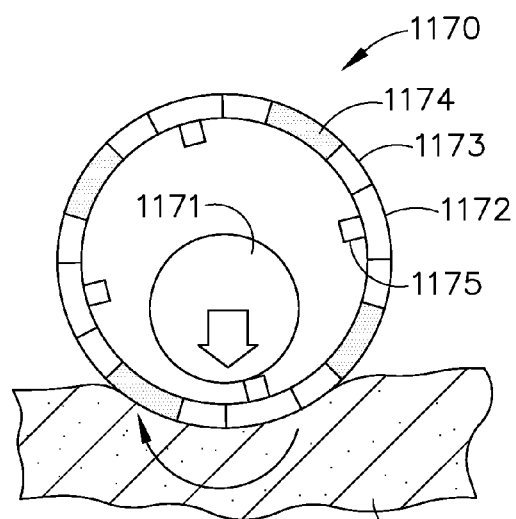
FIG. 30B depicts a cross-sectional end view of the end effector of FIG. 29 pressed against tissue.
Figure 31B:
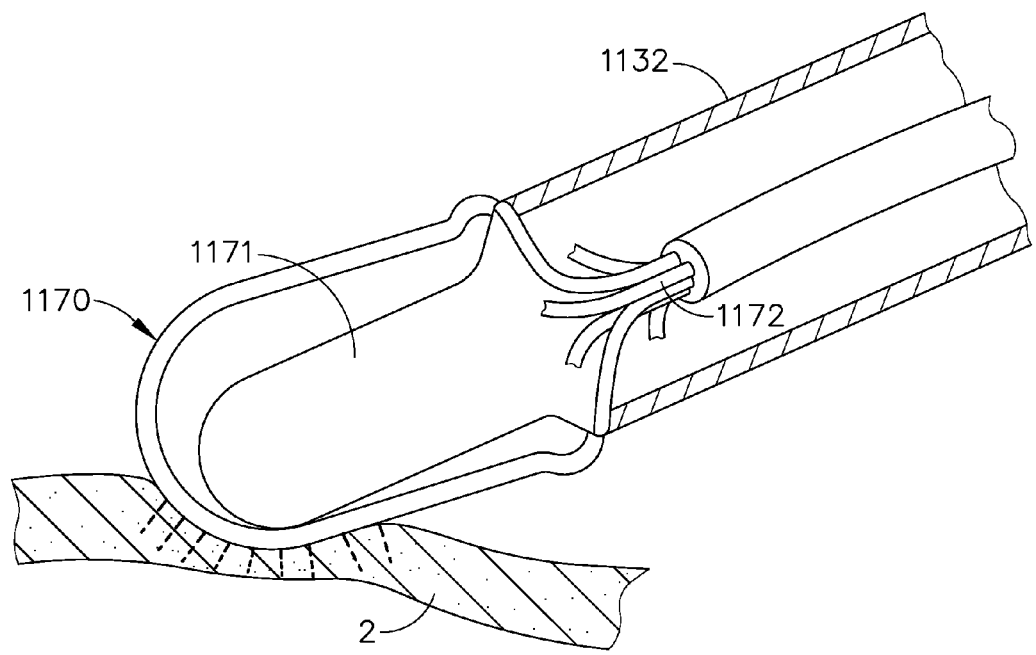
FIG. 31B depicts a cross-sectional side view of the end effector of FIG. 29 pressed against tissue.

In an exemplary use, end effector (1140) is coupled to sheath (1132), as shown in FIG. 29. End effector (1140) is inserted into a patient via a trocar. If a small bleeding source is detected, tip (1170) may be placed on the small bleeding source and end effector (1140) may deliver RF energy to electrosurgically seal the tissue. When tip (1170) is applied to tissue (2), tip (1170) deforms, as shown in FIGS. 30B and 31B. As tip (1170) deforms, protrusion (1175) of first electrode surface (1172) that is applied to tissue (2) contacts rod (1171). Rod (1171) energizes the selected first electrode surface (1172). When first electrode surface (1172) is energized, RF energy flows through tissue positioned between electrode surfaces (1172, 1174). The bipolar RF energy delivered by power source (80) ultimately welds the tissue layer portions. When tip (1170) is removed from tissue (2), tip (1170) resiliently deforms back to the original position, as shown in FIGS. 30A and 31A. This decouples first electrode surface (1172) from rod (1171) to de-energize end effector (1140). Tip (1170) may then be placed on another area of tissue to seal the tissue.

III. Miscellaneous

It should be understood that any of the versions of electrosurgical instrument (10) described herein may include various other features in addition to or in lieu of those described above. By way of example only, any of the devices herein may also include one or more of the various features disclosed in any of the various references that are incorporated by reference herein.

It should also be understood that any of the devices described herein may be modified to include a motor or other electrically powered device to drive an otherwise manually moved component. Various examples of such modifications are described in U.S. Pub. No. 2012/0116379, entitled "Motor Driven Electrosurgical Device with Mechanical and Electrical Feedback," published May 10, 2012, now U.S. Pat. No. 9,161,803, issued Oct. 20, 2015, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410, 603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
   (a) an end effector, wherein the end effector comprises:
      (i) an upper jaw,
      (ii) a lower jaw, wherein the upper jaw is configured to pivot relative to the lower jaw,
      (iii) a first electrical contact, and
      (iv) a second electrical contact; and
   (b) an electrode cap, wherein the electrode cap is selectively coupled to one of either the upper or lower jaw, wherein the electrode cap comprises:
      (i) a first electrode surface, wherein the first electrode surface is configured to electrically communicate with the first electrical contact when the electrode cap is selectively coupled to one of either the upper or lower jaw, wherein the first electrode surface is configured to operate at a first polarity, and
      (ii) a second electrode surface, wherein the second electrode surface is configured to electrically communicate with the second electrical contact when the electrode cap is selectively coupled to one of either the upper or lower jaw, wherein the second electrode surface is configured to operate at a second polarity, wherein the second polarity is opposite to the first polarity;
   wherein the electrode cap is configured to be applied to tissue, wherein the electrode cap is operable to deliver bipolar RF energy to tissue.

2. The apparatus of claim 1, wherein the electrode cap is coupled to the lower jaw.

3. The apparatus of claim 2, wherein the lower jaw comprises an engagement recess, wherein the electrode cap comprises a protrusion, wherein the protrusion is configured to be inserted within the engagement recess to couple the electrode cap to the lower jaw.

4. The apparatus of claim 1, wherein the first electrode surface and the second electrode surface are positioned to extend along the electrode cap such that the first and second electrode surfaces are substantially parallel.

5. The apparatus of claim 1, wherein the first electrode surface is configured in a waved pattern, wherein a plurality of second electrode surfaces are positioned between peaks in the waved pattern.

6. The apparatus of claim 1, wherein the electrode cap comprises a plurality of first electrode surfaces and a plurality of second electrode surfaces, wherein the first and second electrode surfaces are positioned obliquely across the electrode cap, wherein the first electrode surfaces are configured to alternate with the second electrode surfaces.

7. The apparatus of claim 1, wherein the first electrode surface is positioned in an arc configuration, wherein the second electrode surface is positioned in an arc configuration, wherein the first electrode surface is positioned between the arc of the second electrode surface.

8. The apparatus of claim 1, wherein the first and second electrode surfaces comprise a color changing material configured to provide visual feedback when the first and second electrode surfaces are energized.

9. The apparatus of claim 8, wherein the color changing material is configured to change colors in response to heat.

10. The apparatus of claim 1, wherein the upper and lower jaws are operable to deliver bipolar RF energy to tissue positioned between the upper and lower jaws.

11. The apparatus of claim 1, wherein the first and second electrode surfaces are positioned on a tip of the electrode cap.

12. The apparatus of claim 11, wherein the first electrode surface is recessed relative to the second electrode surface.

13. The apparatus of claim 11, wherein the first electrode surface is resiliently biased to a first position such that the first electrode surface is de-activated, wherein the first electrode surface is configured to translate to a second position such that the first electrode surface is activated.

14. The apparatus of claim 13, wherein the second electrode surface is resiliently biased to a first position such that the second electrode surface is de-activated, wherein the second electrode surface is configured to translate to a second position such that the second electrode surface is activated.

15. The apparatus of claim 11, wherein the first electrode surface is positioned under a sponge, wherein the first electrode surface is activated when the sponge is saturated with bodily fluid.

16. An apparatus for operating on tissue, the apparatus comprising:
(a) an end effector, wherein the end effector comprises:
(i) first jaw comprising a first electrode surface, wherein the first electrode surface is configured to operate at a first polarity, and
(ii) a second jaw, wherein the first jaw is configured to pivot relative to the second jaw, wherein the second jaw comprises a second electrode surface, wherein the second electrode surface is configured to operate at a second polarity, wherein the first polarity is opposite the second polarity; and
(b) an electrode cap, wherein the electrode cap is selectively coupled to one of either the first jaw or the second jaw, wherein the electrode cap comprises:
(i) a third electrode surface, wherein the third electrode surface is in communication with the first electrode surface, and
(ii) a fourth electrode surface, wherein the fourth electrode surface is configured to operate at the second polarity;
wherein the electrode cap is configured to be applied to tissue, wherein the electrode cap is operable to deliver bipolar RF energy to tissue.

17. The apparatus of claim 16, wherein the electrode cap further comprises an insulated layer of film, wherein the insulated layer of film defines an opening to expose the third electrode surface and the fourth electrode surface.

18. The apparatus of claim 16, wherein the third electrode surface forms an annular shape, wherein the fourth electrode surface is coaxially positioned within the third electrode surface.

19. The apparatus of claim 18, wherein the fourth electrode surface is proximal in relation to the third electrode surface.

20. An apparatus for operating on tissue, the apparatus comprising:
(a) an end effector, wherein the end effector comprises:
(i) a first jaw comprising a first electrode surface, wherein the first electrode surface is configured to operate at a first polarity, and
(ii) a second jaw, wherein the first jaw is configured to pivot relative to the second jaw, wherein the second jaw comprises a second electrode surface, wherein the second electrode surface is configured to operate at a second polarity, wherein the first polarity is opposite the second polarity; and
(b) an electrode cap, wherein the electrode cap is selectively coupled to one of either the first jaw or the second j aw, wherein the electrode cap comprises:
(i) a third electrode surface, wherein the third electrode surface configured to electrically communicate with the first electrode surface when the electrode cap is selectively coupled to one of either the first jaw or the second jaw, and
(ii) a fourth electrode surface, wherein the fourth electrode surface is configured to operate at the second polarity, wherein the fourth electrode surface is configured to electrically communicate with the second electrode surface when the electrode cap is selectively coupled to one of either the first jaw or the second jaw;
wherein the electrode cap is configured to be applied to tissue, wherein the electrode cap is operable to deliver bipolar RF energy to tissue.

* * * * *